US012084655B2

(12) United States Patent
Walters et al.

(10) Patent No.: US 12,084,655 B2
(45) Date of Patent: Sep. 10, 2024

(54) PACKAGING OLIGONUCLEOTIDES INTO VIRUS-LIKE PARTICLES

(71) Applicant: CHECKMATE PHARMACEUTICALS, Cambridge, MA (US)

(72) Inventors: Evan David Walters, Brighton, MA (US); Frank Hennecke, Dietlikon (CH)

(73) Assignee: CHECKMATE PHARMACEUTICALS, Cambridge, MA (US)

( * ) Notice: Subject to any disclaimer, the term of this patent is extended or adjusted under 35 U.S.C. 154(b) by 899 days.

(21) Appl. No.: 17/045,929

(22) PCT Filed: Apr. 8, 2019

(86) PCT No.: PCT/IB2019/052867
§ 371 (c)(1),
(2) Date: Oct. 7, 2020

(87) PCT Pub. No.: WO2019/197965
PCT Pub. Date: Oct. 17, 2019

(65) Prior Publication Data
US 2021/0261958 A1   Aug. 26, 2021

Related U.S. Application Data

(60) Provisional application No. 62/654,586, filed on Apr. 9, 2018.

(51) Int. Cl.
*C12N 15/11* (2006.01)
*C12N 7/00* (2006.01)

(52) U.S. Cl.
CPC .............. *C12N 15/111* (2013.01); *C12N 7/00* (2013.01); *C12N 2795/18123* (2013.01)

(58) Field of Classification Search
None
See application file for complete search history.

(56) References Cited

U.S. PATENT DOCUMENTS

| | | | |
|---|---|---|---|
| 3,854,480 A | 12/1974 | Zaffaroni | |
| 4,179,337 A | 12/1979 | Davis et al. | |
| 4,301,144 A | 11/1981 | Iwashita et al. | |
| 4,452,775 A | 6/1984 | Kent et al. | |
| 4,469,863 A | 9/1984 | Ts et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,675,189 A | 6/1987 | Kent et al. | |
| 4,791,192 A | 12/1988 | Nakagawa et al. | |
| 4,816,397 A | 3/1989 | Boss et al. | |
| 4,816,567 A | 3/1989 | Cabilly et al. | |
| 5,023,243 A | 6/1991 | Tullis | |
| 5,075,109 A | 12/1991 | Tice et al. | |
| 5,133,974 A | 7/1992 | Paradissis et al. | |
| 5,177,198 A | 1/1993 | Spielvogel et al. | |
| 5,407,686 A | 4/1995 | Patel et al. | |
| 5,658,738 A | 8/1997 | Nadeau et al. | |
| 5,668,265 A | 9/1997 | Nadeau et al. | |
| 5,703,057 A | 12/1997 | Johnston et al. | |
| 5,736,152 A | 4/1998 | Dunn | |
| 5,759,808 A | 6/1998 | Casterman et al. | |
| 5,770,429 A | 6/1998 | Lonberg et al. | |
| 5,837,243 A | 11/1998 | Deo et al. | |
| 5,859,231 A | 1/1999 | Shaw et al. | |
| 5,916,771 A | 6/1999 | Hori et al. | |
| 5,922,845 A | 7/1999 | Deo et al. | |
| 6,028,182 A | 2/2000 | Uhlmann et al. | |
| 6,160,109 A | 12/2000 | Just et al. | |
| 6,194,388 B1 | 2/2001 | Krieg et al. | |
| 6,207,819 B1 | 3/2001 | Manoharan et al. | |
| 6,218,371 B1 | 4/2001 | Krieg et al. | |
| 6,239,116 B1 | 5/2001 | Krieg et al. | |
| 6,451,563 B1 | 9/2002 | Wittig et al. | |
| 6,451,593 B1 | 9/2002 | Wittig et al. | |
| 6,602,684 B1 | 8/2003 | Umana et al. | |

(Continued)

FOREIGN PATENT DOCUMENTS

| CN | 101479375 A | 7/2009 |
|---|---|---|
| CN | 1599623 B | 5/2011 |

(Continued)

OTHER PUBLICATIONS

International Search Report issued Jul. 5, 2019 in International Appl. No. PCT/IB2019/052867.
Kerkmann et al., "Spontaneous Formation of Nucleic Acid-based Nanoparticles is Responsible for High Interferon-[alpha] Induction by CpG-A in Plasmacytoid Dendritic Cells," Journal of Biological Chemistry 280(9):8086-8093, Mar. 4, 2005.
Affymetrix, A Data Sheet GeneChip Human Genome U133 Arrays The Most Comprehensive Coverage of the Human Genome in Two Flexible Formats: Single-array Cartridges and Multi-array Plates Multi-array Plate Format Power of the Probe Set Content Relationship Between GeneC, 2007.
Ahonen et al., Combined TLR and CD40 Triggering Induces Potent CD8+ T Cell Expansion with Variable Dependence on Type I IFN, Journal of Experimental Medicine, Mar. 15, 2004, vol. 199, No. 6, pp. 775-784.

(Continued)

*Primary Examiner* — Patrick T Lewis
(74) *Attorney, Agent, or Firm* — LATHROP GPM LLP; James V. DeGiulio, Esq.; James H. Velema, Esq.

(57) ABSTRACT

The present invention relates to processes for producing compositions comprising (i) a virus-like particle of an RNA bacteriophage, and (ii) aggregated oligonucleotides, wherein said aggregated oligonucleotides are packaged into said virus-like particle. The invention further provides processes for producing nucleotide compositions comprising aggregated oligonucleotides suitable for use in the aforementioned processes before. Moreover, the invention further provides nucleotide compositions comprising aggregated oligonucleotides. Furthermore, the invention further provides compositions comprising (i) a virus-like particle of an RNA bacteriophage, and (ii) aggregated oligonucleotides, wherein said aggregated oligonucleotides are packaged into said virus-like particle.

10 Claims, 6 Drawing Sheets

Specification includes a Sequence Listing.

(56) References Cited

U.S. PATENT DOCUMENTS

| | | |
|---|---|---|
| 6,682,736 B1 | 1/2004 | Hanson et al. |
| 6,765,087 B1 | 7/2004 | Casterman et al. |
| 6,808,710 B1 | 10/2004 | Wood et al. |
| 6,849,725 B2 | 2/2005 | Junghans et al. |
| 6,949,520 B1 | 9/2005 | Hartmann et al. |
| 7,074,772 B2 | 7/2006 | Wittig et al. |
| 7,410,975 B2 | 8/2008 | Lipford et al. |
| 7,488,802 B2 | 2/2009 | Collins et al. |
| 7,517,520 B2 | 4/2009 | Manolova et al. |
| 7,521,063 B2 | 4/2009 | Klinman et al. |
| 7,566,703 B2 | 7/2009 | Krieg et al. |
| 7,605,238 B2 | 10/2009 | Korman et al. |
| 7,635,468 B2 | 12/2009 | Dobric et al. |
| 7,776,344 B2 | 8/2010 | Hartmann et al. |
| 7,795,235 B2 | 9/2010 | Krieg et al. |
| 7,888,098 B2 | 2/2011 | Richter et al. |
| 7,892,569 B2 | 2/2011 | Klinman et al. |
| 7,943,743 B2 | 5/2011 | Korman et al. |
| 8,017,591 B2 | 9/2011 | Brzezicha et al. |
| 8,198,251 B2 | 6/2012 | Vollmer et al. |
| 8,283,328 B2 | 10/2012 | Krieg et al. |
| 8,304,396 B2 | 11/2012 | Krieg et al. |
| 8,450,467 B2 | 5/2013 | Manoharan et al. |
| 8,541,559 B2 | 9/2013 | Kinzler et al. |
| 8,574,564 B2 | 11/2013 | Renner et al. |
| 8,580,268 B2 | 11/2013 | Debelak et al. |
| 8,586,728 B2 | 11/2013 | Sproat |
| 8,691,209 B2 | 4/2014 | Bachmann et al. |
| 8,691,965 B2 | 4/2014 | Moller |
| 8,728,474 B2 | 5/2014 | Honjo et al. |
| 8,759,305 B2 | 6/2014 | Barrat et al. |
| 8,834,900 B2 | 9/2014 | Krieg et al. |
| 8,940,310 B2 | 1/2015 | Barrat et al. |
| 8,962,579 B2 | 2/2015 | Barrat et al. |
| 8,987,221 B2 | 3/2015 | Zhu et al. |
| 9,126,996 B2 | 9/2015 | Lipford et al. |
| 9,139,554 B2 | 9/2015 | Hope et al. |
| 9,206,430 B2 | 12/2015 | Kandimalla et al. |
| 9,220,683 B2 | 12/2015 | Manoharan et al. |
| 9,260,719 B2 | 2/2016 | Kandimalla et al. |
| 9,404,126 B2 | 8/2016 | Kinzler et al. |
| 9,518,095 B2 | 12/2016 | Emmerling et al. |
| 10,682,365 B2 | 6/2020 | Krieg et al. |
| 10,751,512 B2 | 8/2020 | Yu et al. |
| 2002/0086014 A1 | 7/2002 | Korman et al. |
| 2002/0088014 A1 | 7/2002 | Fang et al. |
| 2003/0086930 A1 | 5/2003 | Mueller et al. |
| 2003/0099668 A1 | 5/2003 | Bachmann et al. |
| 2003/0125279 A1 | 7/2003 | Junghans et al. |
| 2003/0157108 A1 | 8/2003 | Presta |
| 2003/0207336 A1 | 11/2003 | Jardieu et al. |
| 2003/0207346 A1 | 11/2003 | Arathoon et al. |
| 2004/0009949 A1 | 1/2004 | Krieg |
| 2004/0063911 A1 | 4/2004 | Defrees et al. |
| 2004/0072290 A1 | 4/2004 | Umana et al. |
| 2004/0120948 A1 | 6/2004 | Mikayama et al. |
| 2004/0132640 A1 | 7/2004 | Defrees et al. |
| 2004/0142856 A1 | 7/2004 | Defrees et al. |
| 2004/0198680 A1 | 10/2004 | Krieg |
| 2007/0184068 A1 | 8/2007 | Renner et al. |
| 2008/0045473 A1 | 2/2008 | Uhlmann et al. |
| 2009/0082295 A1 | 3/2009 | Jungnelius et al. |
| 2009/0117132 A1 | 5/2009 | Readett et al. |
| 2010/0028504 A1 | 2/2010 | Perry |
| 2010/0098722 A1 | 4/2010 | Bachmann et al. |
| 2010/0285041 A1 | 11/2010 | Uhlmann et al. |
| 2012/0003179 A1 | 1/2012 | Readett et al. |
| 2012/0025149 A1 | 2/2012 | Liang et al. |
| 2012/0219571 A1 | 8/2012 | Vollmer et al. |
| 2012/0301499 A1 | 11/2012 | Bachmann et al. |
| 2013/0012922 A1 | 1/2013 | Klinman et al. |
| 2013/0295110 A1 | 11/2013 | Binder |
| 2014/0163213 A1 | 6/2014 | Debelak et al. |
| 2015/0344884 A1 | 12/2015 | Uhlmann et al. |
| 2017/0175122 A1 | 6/2017 | Guo et al. |
| 2018/0000851 A1 | 1/2018 | Krieg |
| 2018/0169229 A1 | 6/2018 | Yu et al. |
| 2019/0046638 A1 | 2/2019 | Krieg |
| 2020/0281953 A1 | 9/2020 | Krieg et al. |
| 2021/0030783 A1 | 2/2021 | Krieg et al. |
| 2021/0261958 A1 | 8/2021 | Walters et al. |

FOREIGN PATENT DOCUMENTS

| | | |
|---|---|---|
| EP | 0338841 A1 | 10/1989 |
| EP | 0216846 B1 | 1/1990 |
| EP | 0256055 B1 | 8/1991 |
| EP | 0092574 B1 | 4/1992 |
| EP | 0323997 B1 | 4/1993 |
| EP | 1262193 A1 | 12/2002 |
| EP | 3752194 A2 | 12/2020 |
| EP | 3240801 B1 | 1/2021 |
| EP | 3775218 A1 | 2/2021 |
| EP | 3835312 A1 | 6/2021 |
| JP | H10503469 A | 3/1998 |
| JP | 2005-517632 A | 6/2005 |
| JP | 2009-519299 A | 5/2009 |
| JP | 2009-539907 A | 11/2009 |
| WO | WO 1993/000431 A1 | 1/1993 |
| WO | WO 1995/001363 A1 | 1/1995 |
| WO | WO 1996/002555 A1 | 2/1996 |
| WO | WO 1998/018810 A1 | 5/1998 |
| WO | WO 1998/058964 A1 | 12/1998 |
| WO | WO 1999/022764 A1 | 5/1999 |
| WO | WO 2000/006588 A1 | 2/2000 |
| WO | WO 2000/024893 A2 | 5/2000 |
| WO | WO 2000/032231 A1 | 6/2000 |
| WO | WO 2000/037504 A2 | 6/2000 |
| WO | WO 2001/014424 A2 | 3/2001 |
| WO | WO 2001/081405 A2 | 11/2001 |
| WO | WO 2003/024481 A2 | 3/2003 |
| WO | WO 2003/031464 A2 | 4/2003 |
| WO | WO 2004/000351 A1 | 12/2003 |
| WO | WO 2004/007538 A2 | 1/2004 |
| WO | WO 2004/084940 A1 | 10/2004 |
| WO | WO 2005/004907 A1 | 1/2005 |
| WO | WO 2005/117963 A1 | 12/2005 |
| WO | WO 2006/125821 A2 | 11/2006 |
| WO | WO 2007/038720 A2 | 4/2007 |
| WO | WO 2007/039458 A2 | 4/2007 |
| WO | WO 2007/039552 A1 | 4/2007 |
| WO | 2007/068747 A1 | 6/2007 |
| WO | 2007/144150 A1 | 12/2007 |
| WO | WO 2008/073960 A2 | 6/2008 |
| WO | WO 2012/006634 A2 | 1/2012 |
| WO | WO 2014/159990 A1 | 10/2014 |
| WO | WO 2016/011324 A2 | 1/2016 |
| WO | WO 2016/109310 A1 | 7/2016 |
| WO | WO 2017/173334 A1 | 10/2017 |
| WO | 2017/197009 A1 | 11/2017 |
| WO | WO 2019/160866 A2 | 8/2019 |
| WO | WO 2019/197965 A1 | 10/2019 |
| WO | WO 2019/160866 A3 | 5/2020 |
| WO | WO 2023/130072 A1 | 7/2023 |

OTHER PUBLICATIONS

Applicants' remarks for U.S. Appl. No. 15/577,369, filed Apr. 3, 2020, 17 pages.

Arima et al., Cyclodextrin/Dendrimer Conjugates as DNA and Oligonucleotide Carriers, Current Topics in Medicinal Chemistry, 2014, vol. 14, No. 4, pp. 465-477.

Arima, Twenty Years of Research on Cyclodextrin Conjugates with PAMAM Dendrimers Pharmaceutics, May 11, 2021, vol. 13, No. 5, 697.

Assaf et al., A Threshold Level of Tlr9 Mrna Predicts Cellular Responsiveness to Cpg-odn in Haematological and Non-haematological Tumour Cell Lines, Cellular Immunology, 2009, vol. 259, Issue 1, pp. 90-99.

Barnes et al., Characterization Of The Stability Of Recombinant Protein Production In The GS-NS0 Expression System, Biotechnology and Bioengineering, May 20, 2001, vol. 73, No. 4, pp. 261-270.

(56) References Cited

OTHER PUBLICATIONS

Beaucage et al., Synthetic Strategies and Parameters Involved in the Synthesis of Oligodeoxyribonucleotides According to the Phosphoramidite Method, Current Protocols in Nucleic Acid Chemistry, May 2001, Chapter 3, Unit 3.3, pp. 1-20.
Beeh et al., The Novel TLR-9 Agonist QbG10 Shows Clinical Efficacy in Persistent Allergic Asthma, Journal of Allergy and Clinical Immunology, Mar. 2013, vol. 131, No. 3, pp. 866-874.
Bird et al., Single-Chain Antigen-Binding Proteins, Science, Oct. 21, 1988, vol. 242, No. 4877, pp. 423-426.
Bochman et al., DNA Secondary Structures: Stability and Function of G-quadruplex Structures, Nature Reviews Genetics, 2012, vol. 13, pp. 770-780.
Bode et al., CpG DNA as a Vaccine Adjuvant, Expert Review of Vaccines, Apr. 2011, vol. 10, No. 4, pp. 499-511.
Brahmer et al., Safety And Activity Of Anti-PD-L1 Antibody In Patients With Advanced Cancer, New England Journal of Medicine, Jun. 28, 2012, vol. 366, No. 26, pp. 2455-2465.
Brody et al., In Situ Vaccination With a TLR9 Agonist Induces Systemic Lymphoma Regression: A Phase I/II Study Journal of Clinical Oncology, Oct. 1, 2010, vol. 28, No. 28, pp. 4324-4332.
Burnette et al., The Efficacy of Radiotherapy Relies upon Induction of Type I Interferon-Dependent Innate and Adaptive Immunity Cancer Research, Apr. 1, 2011, vol. 71, No. 7, pp. 2488-2496.
Butt et al., Immunosuppressive Networks and Checkpoints Controlling Antitumor Immunity and Their Blockade in the Development of Cancer Immunotherapeutics and Vaccines, Oncogene, Sep. 18, 2014, vol. 33, No. 38, pp. 4623-4631.
Casale et al., CYT003, a TLR9 Agonist, in Persistent Allergic Asthma—a Randomized Placebo-controlled Phase 2b Study, Allergy, 2015, vol. 70, No. 9, pp. 1160-1168.
Chen et al., Oncology Meets Immunology: The Cancer-Immunity Cycle, Immunity, Jul. 25, 2013, vol. 39, No. 1, pp. 1-10.
Chen et al., The Indoleamine 2,3-Dioxygenase Pathway Is Essential for Human Plasmacytoid Dendritic Cell-Induced Adaptive T Regulatory Cell Generation, The Journal of Immunology, Oct. 2008, vol. 181, No. 8, pp. 5396-5404.
Crooke et al., Progress in Antisense Oligonucleotide Therapeutics, Annual Review of Pharmacology and Toxicology, 1996, vol. 36, pp. 107-129.
Donhauser et al., Differential Effects of P-Class Versus Other CpG Oligodeoxynucleotide Classes on the Impaired Innate Immunity of Plasmacytoid Dendritic Cells in HIV Type 1 Infection, AIDS Research and Human Retroviruses, 2010, vol. 26, No. 2, pp. 161-171.
Durand et al., Triple-helix Formation by an Oligonucleotide Containing One (dA)12 and Two (dT)12 Sequences Bridged by Two Hexaethylene Glycol Chains Biochemistry, 1992, vol. 31, No. 38, pp. 9197-9204.
Extended European Search Report Received for EP Patent Application No. 15876030.6, mailed on Jun. 26, 2018, 10 pages.
Extended European Search Report Received for EP Patent Application No. 19754821.7, mailed on Feb. 14, 2022, 12 pages.
Extended European Search Report Received for EP Patent Application No. 21151085.4, mailed on Apr. 23, 2021, 9 pages.
Fontanel et al., Sterical Recognition by T 4 Polynucleotide Kinase of Non-Nucleosidic Moieties 5'-Attached to Oligonucleotides Nucleic Acids Research, 1994, vol. 22, No. 11, pp. 2022-2027.
Fransen et al., Local Immunomodulation for Cancer Therapy: Providing Treatment Where Needed OncoImmunology, Nov. 1, 2013, vol. 2, No. 11, Article No. e26493, pp. 1-3.
Frietze, et al., Engineering Virus-like Particles as Vaccine Platforms, Current Opinion in Virology, 2016, vol. 18, pp. 44-49.
Froehler et al., Triple-Helix Formation by Oligodeoxynucleotides Containing the Carbocyclic Analogs of Thymidine and 5-methyl-2'-Deoxycytidine, Journal of the American Chemical Society, 1992, vol. 114, No. 21, pp. 8320-8322.
Garcia-Martinez et al., Hepatocyte Mitochondrial DNA Drives Nonalcoholic Steatohepatitis by Activation of TLR9 Journal of Clinical Investigation, Mar. 2016, vol. 123, No. 3, pp. 859-864.
GenBank Cytotoxic T-lymphocyte Protein 4 Isoform CTLA-4delTM [Homo Sapiens] GenBank Accession No. NP_001032720.1, Apr. 2, 2019.
GenBank Programmed Cell Death 1 Ligand 1 Isoform a Precursor [Homo Sapiens] Genbank Accession No. NP_054862.1, Mar. 25, 2019.
GenBank Programmed Cell Death 1 Ligand 1 Isoform B Precursor[Homo Sapiens] GenBank Accession No. NP_001254635.1, Mar. 25, 2019.
GenBank Programmed Cell Death Protein 1 Precursor [Homo Sapiens] Genbank Accession No. NP005009.2, Mar. 25, 2019.
Gomes Dos Santos et al., Intraocular Delivery of Oligonucleotides, Current Pharmaceutical Biotechnology, Feb. 2005, vol. 6, No. 1, pp. 7-15.
Gomes et al., Adjusted Particle Size Eliminates the Need of Linkage of Antigen and Adjuvants for Appropriated T Cell Responses in Virus-Like Particle-Based Vaccines Frontiers in Immunology, Mar. 6, 2017, vol. 8, No. 226, 10 Pages.
Gomes et al., Harnessing Nanoparticles for Immunomodulation and Vaccines, Vaccines, 2017, 5(1): 6.
Gong et al., Intratumoral Injection of SD-101, a Novel Interferogenic TLR9 Agonist, Unlocks the Full Potential of PD-1 blockade, Dynavax Technologies, 2015, 1 Page.
Gonnet et al., Exhaustive Matching of the Entire Protein Sequence Database, Science, Jun. 5, 1992, vol. 256, No. 5062, pp. 1443-1445.
Goodchild, Conjugates of Oligonucleotides and Modified Oligonucleotides: A Review of Their Synthesis and Properties, Bioconjugate Chemistry, 1990, vol. 1, No. 3 pp. 165-187.
Grimaldi et al., Abscopal Effects of Radiotherapy on Advanced Melanoma Patients Who Progressed After Ipilimumab Immunotherapy, Oncoimmunology, May 2014, vol. 3, Article No. e28780, 9 Pages.
Hartmann et al., Rational Design of New CpG Oligonucleotides That Combine B Cell Activation With High IFN-α Induction in Plasmacytoid Dendritic Cells, European Journal of Immunology, 2003, vol. 33, No. 6, pp. 1633-1641.
Herbst et al., Predictive Correlates of Response to the Anti-PD-L 1 Antibody MPDL3280A In Cancer Patients, Nature, Nov. 27, 2014, vol. 515, No. 7528, pp. 563-567.
Holliger et al., "Diabodies": Small Bivalent And Bispecific Antibody Fragments, PNAS USA, Jul. 13, 1993, vol. 90, No. 14, pp. 6444-6448.
Hunziker et al., Nucleic Acid Analogues: Synthesis and Properties, Modern Synthetic Methods, 1995, pp. 331-417.
Huston et al., Protein Engineering of Antibody Binding Sites: Recovery of Specific Activity in an Anti-Digoxin Single-Chain Fv Analogue Produced in *Escherichia coli*, PNAS USA, Aug. 1, 1988, vol. 85, No. 16, pp. 5879-5883.
International Preliminary Report on Patentability for corresponding International Application No. PCT/US2015/067269, dated Jul. 13, 2017.
International Preliminary Report on Patentability for International Application No. PCT/US2019/017680, mailed Aug. 27, 2020.
International Preliminary Report on Patentability received for PCT Patent Application No. PCT/US2017/025480, Mailed on Oct. 2, 2018.
International Search Report and Written Opinion received for PCT Patent Application No. PCT/US2015/067269 mailed on Mar. 11, 2016.
International Search Report and Written Opinion received for PCT Patent Application No. PCT/US2017/025480, Mailed on Sep. 11, 2017.
International Search Report and Written Opinion received for PCT Patent Application No. PCT/US2019/017680, mailed on Apr. 19, 2019, 15 pages.
International Search Report and Written Opinion received for PCT Patent Application No. PCT/US2022/082627, mailed on Jun. 20, 2023.
Iyer et al., 3H-1,2-benzodithiole-3-one 1,1-dioxide as an Improved Sulfurizing Reagent in the Solid-phase Synthesis of Oligodeoxyribonucleoside Phosphorothioates, Journal of the American Chemical Society, 1990, vol. 112, No. 3, pp. 1253-1254.

(56) References Cited

OTHER PUBLICATIONS

Jiang et al., Pseudo-cyclic Oligonucleotides: in Vitro and in Vivo Properties, Bioorganic & Medicinal Chemistry, 1999, vol. 7, No. 12, pp. 2727-2735.

Joshi et al., Biodegradable Particles as Vaccine Delivery Systems: Size Matters, The AAPS Journal, Jan. 2013, vol. 15, No. 1, pp. 85-94.

Kapp et al., Genuine Immunomodulation With Dslim, Molecular Therapy Nucleic Acids, Jun. 2014, vol. 3, e170.

Karbach et al., Efficient In vivo Priming by Vaccination with Recombinant NY-ESO-1 Protein and CpG in Antigen Naïve Prostate Cancer Patients, Clinical Cancer Research, Feb. 15, 2011, vol. 17, No. 4, pp. 861-870.

Karbach et al., Tumor-Reactive CD8+ T-cell Responses After Vaccination With NY-ESO-1 Peptide, CpG 7909 and Montanide ISA-51: Association With Survival, International Journal of Cancer, Feb. 15, 2010, vol. 126, No. 4, pp. 909-918.

Kawai, et al. Toll-like Receptors and Their Crosstalk with Other Innate Receptors in Infection and Immunity, Immunity, May 27, 2011, vol. 34, pp. 637-650.

Keler et al., Bispecific Antibody-dependent Cellular Cytotoxicity of HER2/neu-overexpressing Tumor Cells by Fcγ Receptor Type I-expressing Effector Cells, Cancer Research, Sep. 5, 1997, vol. 57, No. 18, pp. 4008-4014.

Kim et al., In Situ Vaccination Against Mycosis Fungoides by Intratumoral Injection of a TLR9 Agonist Combined With Radiation: a Phase 1/2 Study, Blood, Jan. 12, 2012, vol. 119, No. 2, pp. 355-363.

Kim et al., Phase I trial of a Toll-like receptor 9 agonist, PF-3512676 (CPG 7909), in patients with treatment-refractory, cutaneous T-cell lymphoma, Journal of the American Academy of Dermatology, Dec. 2010, vol. 63, Issue 6, pp. 975-983.

Kim et al., The Path to Reactivation of Antitumor Immunity and Checkpoint Immunotherapy, Cancer Immunology Research, Oct. 2014, vol. 2, No. 10, pp. 926-936.

Klimek, et al. Assessment of Clinical Efficacy of CYT003-QbG10 in Patients With Allergic Rhinoconjunctivitis: A Phase IIb Study, Clinical & Experimental Allergy, Jun. 14, 2011, vol. 41, No. 9, pp. 1305-1312.

Kortylewski et al., In Vivo Delivery of siRNA to Immune Cells by Conjugation to a TLR9 Agonist Enhances Antitumor Immune Responses, Nature Biotechnology, Oct. 2009, vol. 27, No. 10, pp. 925-932.

Krieg et al., Induction of Systemic TH1-Like Innate Immunity in Normal Volunteers Following Subcutaneous but Not Intravenous Administration of CPG 7909, a Synthetic B-Class CpG Oligodeoxynucleotide TLR9 Agonist, Journal of Immunotherapy, 2004, vol. 27, No. 6, pp. 460-471.

Krieg et al., P-Chirality-Dependent Immune Activation by Phosphorothioate CpG Oligodeoxynucleotides Oligonucleotides, 2003, vol. 13, No. 6, pp. 491-499.

Krieg, CpG Motifs in Bacterial DNA and their Immune Effects, Annual Review of Immunology, Jan. 1, 2002, vol. 20, No. 1, pp. 709-760.

Krieg, CpG Still Rocks! Update on an Accidental Drug Nucleic Acid Therapeutics, Apr. 2012, vol. 22, No. 2, pp. 77-89.

Krieg, Therapeutic potential of Toll-like receptor 9 activation, Nat. Rev. Drug Discov., 2006, 5(6): 471-484.

Krug et al., Identification of CpG oligonucleotide sequences with high induction of IFN-alpha/beta in plasmacytoid dendritic cells, Eur. J. Immunol., Jul. 2001, 31(7): 2154-2163.

Kruit et al., Selection of Immunostimulant AS15 for Active Immunization With MAGE-A3 Protein: Results of a Randomized Phase II Study of the European Organisation for Research and Treatment of Cancer Melanoma Group in Metastatic Melanoma, Journal of Clinical Oncology, Jul. 1, 2013, vol. 31, No. 19, pp. 2413-2420.

Kuroiwa et al., Manipulation of Human Minichromosomes to Carry Greater Than Megabase-sized Chromosome Inserts, Nature Biotechnology, 2000, vol. 18, pp. 1086-1090.

Langer, New Methods of Drug Delivery, Science, Sep. 28, 1990, vol. 249, No. 4976, pp. 1527-1533.

Lemke et al., Combination Lymphoma Immunotherapy Using Checkpoint Blockade and Intratumoral Virus-like Particles Containing CpG TLR9 Agonist, Blood, Dec. 2, 2016, vol. 128, No. 22, 3 Pages.

Linehan et al., "A minimal RNA ligand for potent RIG-I activation in living mice", Sci Adv., Feb. 21, 2018, 4: e1701854.

Link et al., Oligodeoxynucleotide CpG 7909 Delivered as Intravenous Infusion Demonstrates Immunologic Modulation in Patients With Previously Treated Non-Hodgkin Lymphoma, Journal of Immunotherapy, 2006, vol. 29, No. 5, pp. 558-568.

Lombardi et al., Plasmacytoid Dendritic Cells, a Role in Neoplastic Prevention and Progression European Journal of Clinical Investigation, 2015, vol. 45, No. S1, pp. 1-8.

Lonberg et al., Antigen-specific Human Antibodies From Mice Comprising Four Distinct Genetic Modifications, Nature, 1994, vol. 368, pp. 856-859.

Lovgren et al., Enhanced Cytotoxicity and Decreased CD8 Dependence of Human Cancer-specific Cytotoxic T Lymphocytes After Vaccination With Low Peptide Dose Cancer Immunology, Immunotherapy, Jun. 2012, vol. 61, No. 6, pp. 817-826.

Lu, TLR Agonists for Cancer Immunotherapy: Tipping the Balance between the Immune Stimulatory and Inhibitory Effects, Frontiers in Immunology, 2014, vol. 5, Article No. 83, 4 Pages.

Lukacs-Kornek, et al. Dendritic Cells in Liver Injury and Fibrosis: Shortcomings and Promises Journal of Hepatology, 2013, vol. 59, No. 5, pp. 1124-1126.

Luke, Abstract CT032: CMP-001 Demonstrates Improved Response in Noninflamed Anti-PD-1 Refractory Melanoma and Response is Associated With Serum CXCL10, Cancer Research, No. 13, 2021 vol. 81, Issue 13 supplement: CT032.

Mangsbo et al., Enhanced Tumor Eradication by Combining CTLA-4 or PD-1 Blockade with CpG Therapy Journal of Immunotherapy, Apr. 1, 2010, vol. 33, No. 3, pp. 225-235.

Manolova et al., Nanoparticles Target Distinct Dendritic Cell Populations According to Their Size European Journal of Immunology, 2008, vol. 38, No. 5, pp. 1404-1413.

Marshall et al., Identification of a Novel CpG DNA Class and Motif That Optimally Stimulate B Cell and Plasmacytoid Dendritic Cell Functions, Journal of Leukocyte Biology, 2003, vol. 73, No. 6, pp. 781-792.

Marshall et al., Novel Chimeric Immunomodulatory Compounds Containing Short CpG Oligodeoxyribonucleotides Have Differential Activities in Human Cells, Nucleic Acids Research, Sep. 1, 2003, vol. 31, No. 17, pp. 5122-5133.

Marshall et al., Superior Activity of the Type C Class of ISS In Vitro and In Vivo Across Multiple Species, DNA Cell Biol., 2005, vol. 24, No. 2, pp. 63-72.

Mason et al., Molecular Targeting of Toll-like Receptor 9 With CpG oligodeoxynucleotides (ODN) for Enhancement of Tumor Radioresponse, International Journal of Radiation Oncology, Biology, Physics, Sep. 2004, vol. 60, Issue 1 Supplement S346: 1 Page.

Mathan et al., Human Plasmacytoid Dendritic Cells: From Molecules to Intercellular Communication Network, Frontiers in Immunology, Nov. 12, 2013, vol. 4, pp. 1-16.

Matteucci et al., The Synthesis of Oligodeoxyprimidines on a Polymer Support, Tetrahedron Letters, 1980, vol. 21, No. 8, pp. 719-722.

Millward et al., Phase I Study of Tremelimumab (CP-675 206) Plus PF-3512676 (CPG 7909) in Patients With Melanoma or Advanced Solid Tumours, British Journal of Cancer, May 28, 2013, vol. 108, No. 10 pp. 1998-2004.

Mohsen et al., Delivering Adjuvants and Antigens in Separate Nanoparticles Eliminates the Need of Physical Linkage for Effective Vaccination, Journal of Controlled Release, 2017, vol. 251, pp. 92-100.

Molenkamp et al., Intradermal CpG-B Activates Both Plasmacytoid and Myeloid Dendritic Cells in the Sentinel Lymph Node of Melanoma Patients, Clinical Cancer Research, May 15, 2007, vol. 13, No. 10 pp. 2961-2969.

(56) References Cited

OTHER PUBLICATIONS

Moseman, et al. Human Plasmacytoid Dendritic Cells Activated by CpG Oligodeoxynucleotides Induce the Generation of CD4+CD25+ Regulatory T Cells, The Journal of Immunology, Oct. 1, 2004, vol. 173, No. 7 pp. 4433-4442.

Mumm et al., Pegylated IL-10 Induces Cancer Immunity: the Surprising Role of IL-10 as a Potent Inducer of IFN-γ-mediated CD8+T Cell Cytotoxicity, BioEssays, Jul. 2013, vol. 35, No. 7, pp. 623-631.

Nielsen et al., Peptide Nucleic Acid (PNA). A DNA Mimic With a Peptide Backbone, Bioconjugate Chemistry, 1994, vol. 5, No. 1 pp. 3-7.

Nierkens et al., Route of Administration of the Tlr9 Agonist Cpg Critically Determines the Efficacy of Cancer Immunotherapy in Mice, PLOS One, Dec. 18, 2009, vol. 4, No. 12, Article No. e8368, pp. 1-9.

Ortigao et al., Antisense Effect of Oligodeoxynucleotides with Inverted Terminal Internucleotidic Linkages: A Minimal Modification Protecting against Nucleolytic Degradation, Antisense Research and Development, 1992, vol. 2, No. 2, pp. 129-146.

Partial Supplementary European Search Report Received in European Patent Application No. 19754821.7, Mailed on Nov. 11, 2021, 16 pages.

Pearson, Flexible Sequence Similarity Searching with the FASTA3 Program Package, Methods in Molecular Biology, 2000, vol. 132, pp. 185-219.

Pearson, Rapid and sensitive sequence comparison with FASTP and FASTA, Methods in Enzymology, 1990, vol. 183, pp. 63-98.

Pearson, Using the FASTA Program to Search Protein and DNA Sequence Databases, Methods in Molecular Biology, 1994, vol. 24, pp. 307-331.

Poljak, Production and Structure of Diabodies, Structure, Dec. 15, 1994, vol. 2, No. 12, pp. 1121-1123.

Postow et al., Immunologic Correlates of the Abscopal Effect in a Patient with Melanoma, The New England Journal of Medicine, Mar. 8, 2012, vol. 366, No. 10, pp. 925-931.

Powles et al., MPDL3280A (Anti-PD-L1) Treatment Leads to Clinical Activity in Metastatic Bladder Cancer, Nature, vol. 515, No. 7528 pp. 558-562. Nov. 27, 2014.

Prasanna et al., Exploiting Sensitization Windows of Opportunity in Hyper and Hypo-fractionated, Radiation Therapy Journal of Thoracic Disease, Apr. 2014, vol. 6, No. 4, pp. 287-302.

Qi et al., CpG oligodeoxynucleotide induces apoptosis and cell cycle arrest in A20 lymphoma cells via TLR9-mediated pathways, Mol. Immun., 2013, 54(3): 327-337.

Rajasagi et al., Systematic Identification of Personal Tumor-specific Neoantigens in Chronic Lymphocytic Leukemia, Blood, Jul. 17, 2014, vol. 124, No. 3, pp. 453-462.

Ribas, et al., Overcoming PD-1 Blockade Resistance with CpG-A Toll-Like Receptor 9 Agonist Vidutolimod in Patients with Metastatic Melanoma, Cancer Discovery, Dec. 2021, vol. 11, No. 12, pp. 2998-3007.

Sabree, et al., Direct and Indirect Immune Effects of CMP-001, a Virus-like Particle Containing a TLR9 Agonist, The Journal for ImmunoTherapy of Cancer, 2021, vol. 9, No. 6, pp. 1-13.

Sabree, et al., Monocytes Exposed to Immune Complexes Reduce pDC Type 1 Interferon Response to Vidutolimod, Vaccines, Sep. 2, 2021, vol. 9, No. 9, pp. 1-12.

Sato et al., Interleukin 10 in the Tumor Microenvironment: A Target for Anticancer Immunotherapy, Immunologic Research, Dec. 2011, vol. 51, No. 2-3, pp. 170-182.

Schifferli et al., Physiological and Pathological Aspects of Circulating Immune Complexes, Kidney International, Apr. 1989, vol. 35, No. 4, pp. 993-1003.

Schmidt et al., Cytokine and Ig-production by CG-containing Sequences With Phosphorodiester Backbone and Dumbbell-shape, 2006, Allergy, vol. 61, pp. 56-63.

Seliger et al., Oligonucleotide Analogues with Terminal 3'-3'- and 5'-5'- Internucleotidic Linkages as Antisense Inhibitors of Viral Gene Expression, Nucleosides and Nucleotides, 1991, vol. 10, Issue 1-3, pp. 469-475.

Sergueev et al., H-Phosphonate Approach for Solid-Phase Synthesis of Oligodeoxyribonucleoside Boranophosphates and Their Characterization, Journal of the American Chemical Society, 1998, vol. 120, No. 37, pp. 9417-9427.

Sharma et al., Nucleic Acid-Sensing Receptors: Rheostats of Autoimmunity and Autoinflammation, Journal of Immunology, 2015, vol. 195, No. 8, pp. 3507-3512.

Siegal et al., The Nature of the Principal Type 1 Interferon-Producing Cells in Human Blood, Science, 1999, vol. 284, No. 5421, pp. 1835-1837.

Sojar et al., A Chemical Method for the Deglycosylation of Proteins, Archives of Biochemistry and Biophysics, Nov. 15, 1987, vol. 259, No. 1, pp. 52-57.

Somasundaram et al., Development of a Trispecific Antibody Conjugate That Directs Two Distinct Tumor-associated Antigens to CD64 on Myeloid Effector Cells, Human Antibodies, 1999, vol. 9, No. 1, pp. 47-54.

Speiser et al., Consensus Statement: Childhood Obesity, The Journal of Clinical Endocrinology & Metabolism, Mar. 2005, vol. 90, No. 3, pp. 1871-1887.

Speiser et al., Memory and Effector CD8 T-cell Responses After Nanoparticle Vaccination of Melanoma Patients, Journal of Immunotherapy, 2010, vol. 33, No. 8, pp. 848-858.

Speiser et al., Rapid and Strong Human CD8+ T Cell Responses to Vaccination With Peptide, IFA, and CpG Oligodeoxynucleotide 7909, Journal of Clinical Investigation, Mar. 2005, vol. 115, No. 3, pp. 739-746.

Stirchak et al., Uncharged Stereoregular Nucleic Acid Analogs: 2. Morpholino Nucleoside Oligomers With Carbamate Internucleoside Linkages, Nucleic Acids Research, 1989, vol. 17, No. 15, pp. 6129-6141.

Tarhini et al., Differing Patterns of Circulating Regulatory T-Cells and Myeloid Derived Suppressor Cells in Metastatic Melanoma Patients Receiving Anti-CTLA4 Antibody and Interferon-α or TLR-9 Agonist and GM-CSF with Peptide Vaccination1, Journal of Immunotherapy, Nov. 2012, vol. 35, No. 9, pp. 702-710.

Tarkoy et al., Nucleic Acid Analogues with Constraint Conformational Flexibility in the Sugar-Phosphate Backbone ("Bicyclo-DNA"). Part 1. Preparation of ( 3'S,5'R)-2'- Deoxy-3',5'-ethano-αβ-D-ribonucleosides ("Bicyclonucleosides"), Helvetica Chimica Acta, Feb. 10, 1993, vol. 76, Issue 1, pp. 481-510.

Taube et al., Association of PD-1, PD-1 Ligands, and Other Features of the Tumor Immune Microenvironment With Response to Anti-PD-1 Therapy, Clinical Cancer Research, Oct. 1, 2014, vol. 20, No. 19, pp. 5064-5074.

Theofilopoulos, et al., Immune Complexes in Human Diseases: A Review, The American Journal of Pathology, Aug. 1980, vol. 100, pp. 529-594.

Thornton et al., Protein Structure. Prediction of Progress at Last, Nature, 1991, vol. 354, No. 6349, pp. 105-106.

Thotakura et al., Enzymatic deglycosylation of glycoproteins, Methods Enzymol., Jan. 1, 2009, vol. 138, pp. 350-359.

Tomizuka et al., Double Trans-Chromosomic Mice: Maintenance of Two Individual Human Chromosome Fragments Containing Ig Heavy and K Loci and Expression of Fully Human Antibodies, PNAS USA, Jan. 18, 2000, vol. 97, No. 2 pp. 722-727.

Tumeh et al., PD-1 Blockade Induces Responses by Inhibiting Adaptive Immune Resistance, Nature, Nov. 27, 2014, vol. 515, pp. 568-571.

Uhlmann et al., Antisense Oligonucleotides: A New Therapeutic Principle Chemical Reviews, Jun. 1990, vol. 90, No. 4 pp. 543-584.

Van De Winkel, et al. Human IgG Fc Receptor Heterogeneity: Molecular Aspects and Clinical Implications, Trends in Immunology, 1993, vol. 14, No. 5 pp. 215-221.

Vandendriessche et al., Acyclic Oligonucleotides: Possibilities and Limitations, Tetrahedron, 1993, vol. 49, No. 33, pp. 7223-7238.

Vicari et al., Interleukin-10 in Viral Diseases and Cancer: Exiting the Labyrinth?, Immunological Reviews, 2004, vol. 202, pp. 223-236.

(56) References Cited

OTHER PUBLICATIONS

Vollmer et al., Immunotherapeutic Applications of CpG oligodeoxynucleotide TLR9 Agonists, Advanced Drug Delivery Reviews, Mar. 28, 2009, vol. 61, Issue 3, pp. 195-204.

Vollmer, et al., Characterization of Three CpG Oligodeoxynucleotide Classes With Distinct Immunostimulatory Activities, European Journal of Immunology, 2004, vol. 34, pp. 251-262.

Ward et al., Binding Activities Of A Repertoire Of Single Immunoglobulin Variable Domains Secreted From *Escherichia coli*, Nature, Oct. 12, 1989, vol. 341, No. 6242, pp. 544-546.

Winter et al., Humanized Antibodies, Immunology Today, Jun. 1, 1993, vol. 14, No. 6 pp. 243-246.

Wong et al., TLR-9 Signaling and Tcr Stimulation Co-regulate CD8(+) T cell-associated PD-1 expression, Immunology Letters, Dec. 2, 2009, vol. 127, Issue 1, pp. 60-67.

Wright, et al., Genetically Engineered Antibodies: Progress And Prospects, Critical Reviews In Immunology, Jan. 1, 1992, vol. 12, No. 3-4, pp. 125-168.

Zeidler et al., Simultaneous Activation of T Cells and Accessory Cells by a New Class of Intact Bispecific Antibody Results in Efficient Tumor Cell Killing, Journal of Immunology, Aug. 1, 1999, vol. 163, No. 3, pp. 1246-1252.

Zitvogel et al., Mechanism of Action of Conventional and Targeted Anticancer Therapies: Reinstating Immunosurveillance, Immunity, Jul. 25, 2013, vol. 39, pp. 74-88.

Andtbacka et al., "Talimogene Laherparepvec Improves Durable Response Rate in Patients With Advanced Melanoma", Journal of Clinical Oncology, Sep. 1, 2015, 33(25): 2780-2788.

Cytos, "Startup to Develop Cytos' Lead Candidate CYT003 as Cancer Immunotherapy", Genetic Engineering and Biotechnology News, Aug. 12, 2015, Retrieved from url: <https://www.genengnews.com/news/startup-to-develop-cytos-lead-candidate-cyt003-as-cancer-immunotherapy/>.

Gursel et al., "Differential and competitive activation of human immune cells by distinct classes of CpG oligodeoxynucleotide", J Leukoc Biol., May 1, 2002, 71(5): 813-820.

Hu et al., "A phase I study of OncoVEXGM-CSF, a second-generation oncolytic herpes simplex virus expressing granulocyte macrophage colony-stimulating factor", Clin Cancer Res., Nov. 15, 2006, 12(22): 6737-6747.

Verthelyi et al., "Human peripheral blood cells differentially recognize and respond to two distinct CPG motifs", Journal of Immunology, Feb. 15, 2001, 166(4): 2372-2377.

PACKAGING OLIGONUCLEOTIDES INTO VIRUS-LIKE PARTICLES

REFERENCE TO AN ELECTRONIC SEQUENCE LISTING

The contents of the electronic sequence listing (01920060US1seqlist.txt; Size: 24 KB; and Date of Creation Sep. 4, 2020) is herein incorporated by reference in its entirety. The present invention relates to processes for producing compositions comprising (i) a virus-like particle of an RNA bacteriophage, and (ii) aggregated oligonucleotides, wherein said aggregated oligonucleotides are packaged into said virus-like particle. The invention further provides processes for producing nucleotide compositions comprising aggregated oligonucleotides suitable for use in the aforementioned processes before. Moreover, the invention further provides nucleotide compositions comprising aggregated oligonucleotides. Furthermore, the invention further provides compositions comprising (i) a virus-like particle of an RNA bacteriophage, and (ii) aggregated oligonucleotides, wherein said aggregated oligonucleotides are packaged into said virus-like particle.

RELATED ART

Virus-like particles of RNA bacteriophages packaged with oligonucleotides, in particular guanine (G)-rich oligonucleotides, are suggested as potent stimulators of the immune system. Such virus-like particles and oligonucleotides packaged therein and processes for their production have been described, for example, in WO2003/024481, WO2004/000351, WO2004/084940, WO2004/007538, WO2007/068747 and WO2007/144150, the entire disclosures of which are incorporated by reference herein. Typically, the processes are based on the disassembly of a recombinant virus-like particle of RNA bacteriophage, the purification of the coat protein of said virus-like particle and the reassembly of said coat protein in the presence of the oligonucleotides leading to the virus-like particles packaged with the oligonucleotides. Efficient and scalable processes for the production of recombinant virus-like particles of RNA bacteriophages are further disclosed, for example, in WO2005/117963, WO2006/125821 and WO2007/039552, which are incorporated herein by reference in its entirety.

Methods of oligonucleotide synthesis have been available for over thirty years with the synthesis through phosphoramidite chemistry being the most commonly used method thereof (Beaucage et al., Curr Protoc Nucleic Acid Chem 3.3.1-3.3.20 (2000), the entire disclosure of which is incorporated herein by reference). There have been many significant improvements to phosphoramidite synthesis to reduce synthesis time and generate higher yield of products. The synthesis of guanine (G)-rich oligonucleotides, in particular the ones with consecutive guanine residues, was always more challenging to achieve at large manufacturing scale, in particular at high purity and high yields, likely due to the poor accessibility of the 5'-hydroxyl group by the activated phosphoramidite in the coupling step. In particular, the support-bound protected G-rich oligomer can form secondary structures and have solubility issues after a certain length leading to impurities and synthesis failures most dominantly leading to oligonucleotide sequences with lower number of G residues or even higher G residues as desired. As a consequence, the purity of the commercially available guanine (G)-rich oligonucleotides has benefited significantly from said improvements made to phosphoramidite synthesis. Thus, while a purity of 60-80% for said guanine (G)-rich oligonucleotide had occasionally been accepted 10-20 years ago, a purity as high as 93%, 95%, or even as high as 97 or 99% in analogy to the non-guanine (G)-rich oligonucleotides, is nowadays generally feasible. Moreover, if said (G)-rich oligonucleotides are part of pharmaceutical drugs, the use of such higher purity (G)-rich oligonucleotides is required and requested for regulatory approval.

G-rich oligonucleotides, in particular those with poly(G)s at the 5' and 3' end and further comprising unmethylated CG dinucleotide motifs and a central palindrome, have the tendency to self-assemble to higher order secondary and tertiary structures via G-tetrad formation of their poly(G) motifs (Kerkmann, M. et al., J. Biol. Chem., (2005) 280(9), 8086-93, Bochman, M L et al. Nat Rev Genet., (2012) 13(11): 770-780; the entire disclosures of which are incorporated by reference herein). These G-quadruplexes can form via inter or intra molecular pathway and are very stable secondary structures. As a result, the size and shape and conformation of these quadruplexes can be quite variable depending on the reaction pathway.

WO2007/144150 describes a process for producing compositions comprising guanine (G)-rich oligonucleotides packaged into virus-like particles of an RNA bacteriophage, wherein the self-assembly of the coat protein of the RNA bacteriophage is performed in the presence of oligonucleotide aggregates which have been obtained by a disaggregation/aggregation process. The aggregation state of the oligonucleotide is characterized by the relative peak start time (PST) in size exclusion HPLC using the capsid of said RNA bacteriophage as standard and PST's of 50 to 110%, preferably of 80 to 95%, has been found to be optimal. It is indicated that such PSTs correspond to oligonucleotide aggregates having an apparent molecular weight in the range of the apparent molecular weight of the capsid of said RNA bacteriophage or slightly below. Despite its improvements over the known processes for producing compositions comprising guanine (G)-rich oligonucleotides packaged into virus-like particles of RNA bacteriophages, the present inventors have identified substantial disadvantages of this prior art process of WO2007/144150.

SUMMARY OF THE INVENTION

In particular, it has been found by the present inventors that aggregated oligonucleotides prepared in accordance with the prior art process of WO2007/144150 and being in accordance with the size distribution as defined in WO2007/144150 showed substantial inconsistencies and large variations with respect to the specific size and conformation of the formed aggregated oligonucleotides, as determined by Dynamic Light Scattering (DLS). In addition, said inconsistencies with respect to the specific size and conformation of the formed aggregated oligonucleotides led further to substantial inconsistencies in the virus-like particles packaged with said aggregated oligonucleotides causing not only the formation of the desired spherical packaged VLPs, but in addition the formation of malformed rod-like aggregates or higher order aggregates. Moreover, said resulting VLPs packaged with said highly polydispersed aggregated oligonucleotides showed not only a lower purity but further an increased instability.

Importantly, it has further been found that the prior art disaggregation/aggregation process of WO2007/144150 is highly dependent on the initial purity of the oligonucleotides used for said disaggregation/aggregation steps. In particular, it has been found that the initial purity of the oligonucleotides used in the disaggregation/aggregation process of WO2007/144150 has an impact on the aggregation of the oligonucleotides, i.e. on the rate of aggregation and, thus, the G-quadruplex formation, to form the defined desired size and conformation of the aggregated oligonucleotides. Typically, the higher the purity of the oligonucleotides used in the disaggregation/aggregation process of WO2007/144150, the faster and more uncontrolled and chaotic the aggregation occurred resulting in an increased amount of typically very large aggregated oligonucleotides outside the desired size window. As a consequence, and since the resulting aggregated oligonucleotides cannot be properly packaged, the final oligonucleotides-packaged-VLPs had a decreased purity requiring intense and costly purification and a decreased stability as evidenced by the change in the SEC chromatogram overtime. Specifically, an increase in low molecular weight peaks were observed overtime suggesting that some of the VLPs were not stable and released the originally packaged DNA and oligonucleotides, respectively, Based on the findings by the inventors and, in particular, based on the large dependency on the purity of the initially used oligonucleotides for the disaggregation/aggregation process of WO2007/144150, it appeared that the processes of WO2007/144150, in particular the disaggregation/aggregation processes of WO2007/144150, have been developed and optimized for lower purity G-rich oligonucleotides. As indicated, not only are high purity G-rich oligonucleotides nowadays ubiquitously available, but, furthermore, their use for pharmaceutical drugs is a prerequisite for regulatory approval. Moreover, a further substantial disadvantage of the prior art processes of WO2007/144150, beside its inconsistencies and large variations with respect to the specific size and conformation of the formed aggregated oligonucleotides depending on the purity of the initially used oligonucleotides, is the herewith associated very narrow time window to achieve the preparation of the aggregated oligonucleotides in the defined size range due to the uncontrolled and chaotic aggregation.

As a consequence and due to these occurring inconsistencies and variations and the strong dependency on the purity of the initially used oligonucleotides, the processes of WO2007/144150 are not suitable for manufacturing at scale, and in particular, not suitable for GMP manufacturing especially for clinical trial material where batch to batch consistency is critical.

Therefore, the present invention provides processes for producing a nucleotide composition comprising aggregated oligonucleotides and for producing a composition comprising a virus-like particle of an RNA bacteriophage and aggregated oligonucleotides packaged in said virus-like particle, thus avoiding or reducing the disadvantages of the prior art processes.

Thus, in a first aspect, the present invention provides for a process for producing a nucleotide composition comprising aggregated oligonucleotides said process comprising the steps of:

(a) providing oligonucleotides, wherein said oligonucleotides comprise at least one poly G stretch;
(b) denaturing said oligonucleotides, wherein said denaturing comprises the step of
  (i) incubating an aqueous solution I comprising said oligonucleotides and a chaotropic agent at a temperature I until the average diameter of said oligonucleotides is 1 nm or less, wherein said average diameter is determined by Dynamic Light Scattering (DLS), and wherein said temperature I is 75° C. to 99° C., and wherein preferably said chaotropic agent is urea;
(c) aggregating said oligonucleotides, wherein said aggregating comprises the steps of
  (i) incubating an aqueous solution II comprising said oligonucleotides having said average diameter of 1 nm or less obtained in step (b), a chaotropic agent and a cation at a temperature II to form said aggregated oligonucleotides, wherein said incubating is performed until the average diameter of said formed aggregated oligonucleotides is 6-16 nm, wherein said average diameter is determined by Dynamic Light Scattering (DLS), and wherein said temperature II is 75° C. to 99° C., and wherein preferably said chaotropic agent is urea;
  (ii) adjusting the temperature of said solution II to a temperature III, wherein said temperature III is below 40° C., preferably below 30° C.;
wherein said steps are preferably performed in the given order.

Advantageously, the inventive processes allow the control of the size of the formed aggregated oligonucleotides, and, hereby, the conformation of aggregated oligonucleotides, and as a consequence thereof, the consistent formation of highly pure, stable and well-formed, namely typically exclusively spherical VLPs packaged with oligonucleotides.

Thus, the inventive processes allow control of the size of the aggregated oligonucleotides by their diameter of between 6-16 nm, preferably 7-14 nm, further preferably 8-14 nm, again further preferably 9-14 nm, again further preferably 10-14 nm, again further preferably 11-13 nm, thus 11, 12 or 13 nm, and most preferably 12 nm, wherein said diameter is determined by Dynamic Light Scattering (DLS).

Importantly, the inventive processes allow not only control of the size and thus, the conformation of the formed aggregated oligonucleotides, but in addition to do so regardless of the purity of the oligonucleotides used for the denaturing step. Furthermore, the inventive processes further enable and provides a wider operating window in which to perform the aggregation step as it allows control of the aggregation. Such control and additional time and wider operating window, respectively, as well as the higher preciseness in the process controls, make the inventive processes highly beneficial for the costly production in GMP quality, in particular large-scale GMP quality. Moreover, the yield of the final obtained oligonucleotide-packaged-VLPs is additionally much higher and more pure, in particular, without the need of further costly purification steps.

As indicated, the prior art processes of WO2007/144150 led to the formation of aggregated oligonucleotides that showed substantial inconsistencies and large variations with respect to the specific size and conformation of the formed aggregated oligonucleotides, as determined by Dynamic Light Scattering (DLS), in contrast to the aggregated oligonucleotides formed by the present inventive processes. It has to be noted, however, that the aggregated oligonucleotides formed by the present inventive processes all met the specification criteria of the relative peak start time (PST), in size exclusion HPLC using the capsid of said RNA bacteriophage as standard, as defined in WO2007/144150, even though the corresponding optimal range is slightly shifted. Thus, the preferred aggregated oligonucleotides formed by the present inventive processes do possess a PST as determined accordingly of 90-105%, preferably of 92%-102%.

A further advantage of the inventive processes is the avoidance of salts and, in particular, the use of a chaotropic agent, preferably urea, for the denaturing step as compared to the prior art process of WO2007/144150. As a consequence, the resulting solutions of the inventive processes containing the denatured, typically monomeric, oligonucleotides are stable without the threat of re-aggregation and thus, could be stored for further use. As such, these solutions may be heated or cooled multiple times without forming aggregates, and advantageously, could be frozen for future use. The latter has not been possible for the prior art processes most likely as indicated due to the presence of salt produced during neutralization step required to stop the denaturing step prior to oligonucleotide degradation. Thus, said prepared prior art solutions had to be subsequently used without the possibility of storage.

For the present invention, the aggregation state of the oligonucleotide is characterized by Dynamic Light Scattering (DLS) which measures the time-dependent fluctuations in the scattered light. The hydrodynamic radii and diameters of the aggregated oligonucleotides are then calculated by relating the rate of diffusion of the aggregate through the solvent. Aggregated oligonucleotides comprising an average hydrodynamic diameter of 6-16 nm, preferably 7-14 nm, further preferably 8-14 nm, again further preferably 9-14 nm, again further preferably 10-14 nm, again further preferably 11-13 nm, thus, 11, 12 or 13 nm, and most preferably 12 nm, has been found to be optimal.

Thus, in a further aspect, the present invention provides for a process for producing a composition comprising (i) a virus-like particle, wherein said virus-like particle is a virus-like particle of an RNA bacteriophage, and (ii) aggregated oligonucleotides, wherein said aggregated oligonucleotides are packaged into said virus-like particle, said process comprising the steps of:
(a) generating a mixture, wherein said mixture comprises:
    (i) a coat protein of said RNA bacteriophage;
    (ii) an agent capable of preventing the self-assembly of said coat protein; and
    (iii) aggregated oligonucleotides, wherein said aggregated oligonucleotides comprise oligonucleotides comprising at least one poly G stretch, and wherein said aggregated oligonucleotides have an average diameter of 6-16 nm, wherein said average diameter is determined by Dynamic Light Scattering (DLS);
(b) removing said agent from said mixture; and
(c) allowing said coat protein to self-assemble into a virus-like particle and to package said aggregated oligonucleotides.

In an again further aspect, the present invention provides for a process for producing a composition comprising (i) a virus-like particle, wherein said virus-like particle is a virus-like particle of an RNA bacteriophage, and (ii) aggregated oligonucleotides, wherein said aggregated oligonucleotides are packaged into said virus-like particle, said process comprising the steps of:
(a) generating a mixture, wherein said mixture comprises:
    (i) a coat protein of said RNA bacteriophage;
    (ii) an agent capable of preventing the self-assembly of said coat protein; and
    (iii) aggregated oligonucleotides, wherein said aggregated oligonucleotides comprise oligonucleotides comprising at least one poly G stretch, and wherein said aggregated oligonucleotides are obtainable by the process according to the first aspect of the present invention, and wherein said aggregated oligonucleotides have an average diameter of 6-16 nm, wherein said average diameter is determined by Dynamic Light Scattering (DLS);
(b) removing said agent from said mixture; and
(c) allowing said coat protein to self-assemble into a virus-like particle and to package said aggregated oligonucleotides.

In an again further aspect, the present invention provides for a process for producing a composition comprising (i) a virus-like particle, wherein said virus-like particle is a virus-like particle of an RNA bacteriophage, and (ii) aggregated oligonucleotides, wherein said aggregated oligonucleotides are packaged into said virus-like particle, said process comprising the steps of:
(a) generating a mixture, wherein said mixture comprises:
    (i) a coat protein of said RNA bacteriophage;
    (ii) an agent capable of preventing the self-assembly of said coat protein; and
    (iii) the nucleotide composition comprising said aggregated oligonucleotides, and wherein said nucleotide composition is obtainable by the process for producing a nucleotide composition comprising aggregated oligonucleotides in accordance with the present invention, and wherein said aggregated oligonucleotides comprise oligonucleotides comprising at least one poly G stretch, and wherein said aggregated oligonucleotides have an average diameter of 6-16 nm, wherein said average diameter is determined by Dynamic Light Scattering (DLS);
(b) removing said agent from said mixture; and
(c) allowing said coat protein to self-assemble into a virus-like particle and to package said aggregated oligonucleotides.

During said processes said virus-like particle is formed by self-assembly of coat protein of said RNA bacteriophage in the presence of said aggregated oligonucleotides.

In an again further aspect, the present invention provides for a nucleotide composition comprising aggregated oligonucleotides, wherein said nucleotide composition is obtainable by the process for producing a nucleotide composition comprising aggregated oligonucleotides in accordance with the present invention, wherein preferably said aggregated oligonucleotides have an average diameter of 6-16 nm, preferably 7-14 nm, wherein said average diameter is determined by Dynamic Light Scattering (DLS).

In an again further aspect, the present invention provides for a nucleotide composition comprising aggregated oligonucleotides, wherein said aggregated oligonucleotides have an average diameter of 7-14 nm, wherein said average diameter is determined by Dynamic Light Scattering (DLS).

In an again further aspect, the present invention provides for a composition comprising (i) a virus-like particle of an RNA bacteriophage, and (ii) aggregated oligonucleotides, wherein said aggregated oligonucleotides are packaged into said virus-like particle, wherein said composition is obtainable by a process for producing a composition comprising (i) a virus-like particle, wherein said virus-like particle is a virus-like particle of an RNA bacteriophage, and (ii) aggregated oligonucleotides in accordance with the present invention.

In an again further aspect, the present invention provides for a composition comprising (i) a virus-like particle of an RNA bacteriophage, and (ii) aggregated oligonucleotides, wherein said aggregated oligonucleotides are packaged into said virus-like particle, wherein said aggregated oligonucleotides have an average diameter of 6-16, preferably of 7-14 nm, wherein said average diameter is determined by Dynamic Light Scattering (DLS).

Further aspects and embodiments of the present invention will be become apparent as this description continues.

DESCRIPTION OF FIGURES

FIG. 1A shows denatured high purity G10 oligonucleotide with an average particle diameter of 0.90 nm indicating that the G10 oligonucleotide secondary structures have been disrupted, denaturing is complete, and monomers have been achieved. Multiple scans were performed as shown by the overlapping curves. The average diameter ($D_{hyd}$) and percent of primary peak (mean) of these scans are reported within data box inset in the graph.

FIG. 1B shows the subsequently aggregated G10 oligonucleotides obtained with proper aggregation and a diameter of 12 nm. Multiple scans were performed as shown by the overlapping curves. The average diameter ($D_{hyd}$) and percent of primary peak (mean) of these scans are reported within data box inset in the graph.

DETAILED DESCRIPTION OF THE INVENTION

Figure 1A:
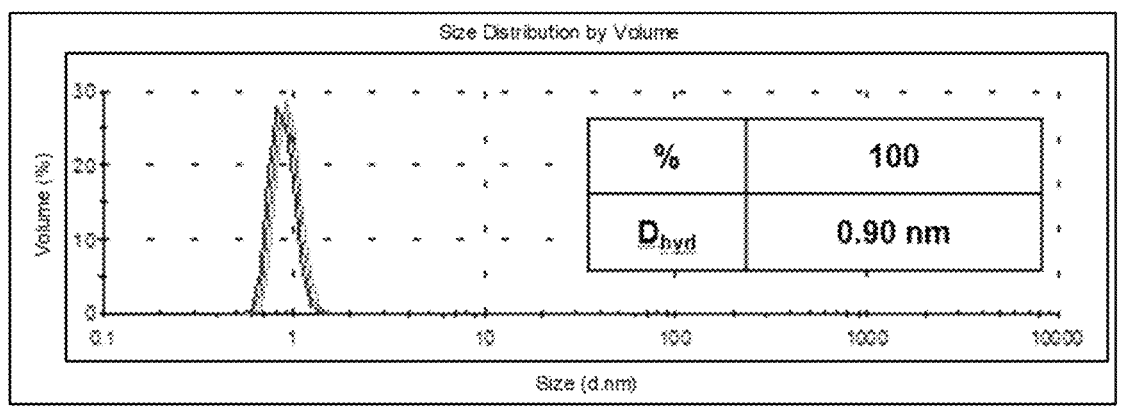
FIG. 1A: Dynamic Light Scattering (DLS) of denatured oligonucleotide G10 and aggregated oligonucleotides G10 as obtained by the inventive process. DLS was performed as described in Example 3.

Unless defined otherwise, all technical and scientific terms used herein have the same meanings as commonly understood by one of ordinary skill in the art to which this invention belongs.

Average diameter: The term "average diameter" as determined by Dynamic Light Scattering (DLS), as used herein, refers to a diameter as measured typically and preferably by DLS in the manner as described in Example 3, and which given average diameter value of measured particles, refers to particles having said diameter as the mean in a normal distribution (Gaussian distribution). Thus, the term "average diameter" as determined by Dynamic Light Scattering (DLS), as used herein, and as typically and preferably applied to the oligonucleotides, aggregated oligonucleotides and VLPs packaged with aggregated oligonucleotides in accordance with the present invention, typically and preferably refers to a diameter as measured by DLS, typically and preferably in the manner as described in Example 3, and which given average diameter value of measured particles, refers to particles, wherein at least 90%, preferably at least 95%, of said particles have a diameter of said given value or a diameter of ±10% of said given value. By way of clarification, for example, an average diameter value of 12 nm of the inventive aggregated oligonucleotides refers to said inventive aggregated oligonucleotides, wherein at least 90%, preferably at least 95%, of said inventive aggregated oligonucleotides have a diameter of 10.8 nm to 13.2 nm. Further, the term "average diameter" as determined by Dynamic Light Scattering (DLS), as used herein, and as typically and preferably applied to the oligonucleotides, aggregated oligonucleotides and VLPs packaged with aggregated oligonucleotides in accordance with the present invention, typically and preferably refers to a diameter as measured by DLS, typically and preferably in the manner as described in Example 3, and which given average diameter value of measured particles, refers to particles, wherein at least 65%, preferably at least 70%, of said particles have a diameter of said given value or a diameter of ±5% of said given value. By way of clarification, for example, an average diameter value of 12 nm of the inventive aggregated oligonucleotides refers to said inventive aggregated oligonucleotides, wherein at least 65%, preferably at least 70%, of said inventive aggregated oligonucleotides have a diameter of 11.4 nm to 12.6 nm.

All ranges of values, in particular all ranges of average diameters or diameters disclosed herein, should refer to all values falling within said range including the values defining the range. By way of clarification, for example, a diameter value of 12 nm to 13 nm should refer to a diameter of 12 nm or 13 nm or all diameters falling within 12 nm and 13 nm.

Chaotropic agent: The term "chaotropic agent" as used herein refers to a molecule or substance that disrupts the ordered structure of a protein, oligonucleotide, or other macromolecule. This decrease in stability is typically caused by the disruption of the hydrogen bonding network. Examples include urea, phenol, isopropyl alcohol (IPA), ethanol and guanidinium chloride amongst others.

Oligonucleotide: The term oligonucleotide as used herein refers to a single stranded deoxyribonucleotide. A preferred oligonucleotide comprises at least one poly G stretch as defined below. More preferred oligonucleotides comprise 2, 3, 4, 5 or 6 of said poly G stretches. Very preferred oligonucleotides comprise exactly two poly G stretches, wherein preferably one of said two poly G stretches is located at the 5' end or at the 3' end of said oligonucleotide. Even more preferred oligonucleotides comprise exactly two poly G stretches, wherein one of said two poly G stretches is located at the 5' end of said oligonucleotide and one of said two poly G stretches is located at the 3' end of said oligonucleotide. Typically and preferably, an oligonucleotide as used herein consists of 6 to 1000, preferably of 10 to 1000, more preferably of 10 to 200, still more preferably of 10 to 100, still more preferably of 20 to 40, and most preferably of 30 nucleotides. Further preferred oligonucleotides consist of 15, 16, 17, 18, 19, 20, 21, 22, 23, 24, 25, 26, 27, 28, 29, 30, 31, 32, 33, 34, 35, 36, 37, 38, 39, or 40 nucleotides. Still more preferred oligonucleotides consists of 24 to 32 nucleotides, more preferably of about 30 nucleotides.

The term oligonucleotide also refers to molecules comprising at least one modified nucleotide, wherein preferably said modified nucleotide is selected from (a) a nucleotide analogue or (b) a nucleotide comprising a backbone modification. In one embodiment the oligonucleotide comprises at least one modified nucleotide selected from the group consisting of (a) peptide nucleic acid, (b) inosin, (c) tritylated bases, (d) phosphorothioates, (e) alkylphosphorothioates, (f) 5-nitroindole desoxyribofuranosyl, (g) 5-methyldesoxycytosine, and (h) 5,6-dihydro-5,6-dihydroxydesoxythymidine. In a further embodiment the oligonucleotide comprises or alternatively consists of phosphorothioated nucleotides. Phosphorothioated nucleotides are protected against degradation in a cell or an organism and are therefore preferred nucleotide modifications. Further preferred are chemically, enzymatically or metabolically modified forms of polynucleotides as typically found in nature. However, preferred oligonucleotides exclusively consists of unmodified nucleotides, i.e. of adenosine, tymidine, guanosine, and/or cytidine. Still further preferred oligonucleotides exclusively consists of phosphodiester bound nucleotides.

Very preferred oligonucleotides are unmethylated CpG containing oligonucleotides comprising at least one, preferably one, two, three or four CpG motifs. Still more preferred oligonucleotides comprise a palindromic sequence, wherein preferably said palindromic sequence comprises least one, preferably one, two, three or four CpG motifs. Still more preferred oligonucleotides comprise a palindromic sequence, wherein preferably said palindromic sequence comprises, or preferably consists of the sequence GAC-GATCGTC (SEQ ID NO:2). Still more preferred oligonucleotides comprise a palindromic sequence, wherein said palindromic sequence is flanked at its 5' end by a poly G stretch and wherein said palindromic sequence is flanked at its 3' end by a poly G stretch, wherein preferably said palindromic sequence is GACGATCGTC (SEQ ID NO:2). Very preferred oligonucleotides comprise a palindromic sequence, wherein said palindromic sequence is flanked at its 5' end by at least 3 to 15, preferably by 6 to 10 guanosine entities and wherein said palindromic sequence is flanked at its 3' end at least 3 to 15, preferably by 6 to 10, guanosine entities, wherein preferably said palindromic sequence is GACGATCGTC (SEQ ID NO:2).

Poly G stretch: The term poly G stretch relates to a segment of an oligonucleotide, wherein said segment consists of at least 3 consecutive guanosine residues. Preferred poly G stretches consist of 3 to 25, preferably of 4 to 20, more preferably of 4 to 15 and most preferably of 4 to 10 consecutive guanosine entities. Further preferred poly G stretches consist of 3, 4, 5, 6, 7, 8, 9, 10, 11, 12, 13, 14, 15, 16, 17, 18, 19, or 20 consecutive guanosine entities.

CpG motif: As used herein, the term CpG motif refers to short DNA sequence, preferably a single stranded DNA sequence, comprising a cytosine (C)—guanosine (G) dinucleotide, wherein C is unmethylated and wherein preferably said CG dinucleotide is phosphodiester bound. Preferably, a CpG motif comprises at least one, preferably one, two or three, additional nucleotides 5' and/or 3' of said CG dinucleotide, wherein further preferably said additional nucleotides do not comprise a CG dinucleotide.

Relative peak start time: The term "relative peak start time" is a parameter which is indicative of the aggregation state of an oligonucleotide and which was analyzed essentially as described in WO 2007/144150 by analytical size exclusion HPLC using the conditions as described in Example 4.

Packaged: The term "packaged" as used herein refers to the state of an oligonucleotide, typically and preferably of aggregated oligonucleotides, in relation to the virus-like particle. The use of the terms "aggregated oligonucleotides packaged into VLP" or "VLP packaged with aggregated oligonucleotides" is equivalent. The term "packaged" as used herein typically and preferably refers to non-covalent binding, preferably to ionic interactions, hydrophobic interactions, or hydrogen bonds. Typically and very preferably, the term "packaged" as used herein refers to the encapsulation of said aggregated oligonucleotides within the VLP. Typically and preferably, a VLP packaged with aggregated oligonucleotides protects said aggregated oligonucleotides from degradation, preferably from DNAse hydrolysis. Therefore, in the preferred meaning, the term "packaged" indicates that the aggregated oligonucleotides in a packaged state are not accessible to DNAse hydrolysis. More preferably, the term "packaged" indicates that the aggregated oligonucleotides are not accessible to DNAse hydrolysis, wherein further preferably the DNAse is DNAseI or Benzonase. Still more preferably, the term "packaged" indicates that the aggregated oligonucleotides are not accessible to Benzonase hydrolysis.

The accessibility of the oligonucleotide for DNAse (e.g. DNaseI or Benzonase) is preferably assayed as described in Examples 11-17 of WO2003/024481A2 (see p. 111 therein). In a preferred meaning, a VLP is regarded as being packaged with an oligonucleotide, when after treatment with Benzonase (190 U Benzonase/mg coat protein in a buffer comprising 2 mM $MgCl_2$, pH 7.2, 20-25° C., 18 h) at least 90%, preferably at least 95%, most preferably at least 98% of said oligonucleotide can be recovered from said VLP (e.g. in an ethidiumbromide stained gel). It is apparent for the artisan that such assays require appropriate controls and may need to be adapted to the specific combination of VLP and oligonucleotide. In a very preferred meaning, oligonucleotide G10 (SEQ ID NO:1) is regarded as being packaged into a VLP of an RNA bacteriophage Qβ, when after treatment with Benzonase (190 U Benzonase/mg coat protein in a buffer comprising 2 mM $MgCl_2$, pH 7.2, 20-25° C., 18 h) at least 90%, preferably at least 95%, most preferably at least 98% of said G10 can be recovered from said VLP of RNA bacteriophage Qβ.

Coat protein: As used herein, the term "coat protein" refers to the protein(s) of a RNA bacteriophage capable of being incorporated within the capsid assembly of the bacteriophage or the RNA bacteriophage. Thus, the term coat protein refers to the protein forming the capsid of a RNA bacteriophage or a VLP of a RNA bacteriophage. Typically and preferably, coat protein of RNA bacteriophages has a dimeric structure.

Fragment of a recombinant coat protein: Fragment of a recombinant coat protein, as used herein, is defined as a polypeptide, which is of at least 70%, preferably at least 80%, more preferably at least 90%, even more preferably at least 95% the length of the wild-type coat protein, or wild type recombinant protein, respectively and which preferably retains the capability of forming VLP. Preferably the fragment is obtained by at least one internal deletion, at least one truncation or at least one combination thereof. The term "fragment of a recombinant coat protein" or "fragment of a coat protein" shall further encompass polypeptide, which has at least 80%, preferably 90%, even more preferably 95% amino acid sequence identity with the wildtype coat protein, respectively, and which is preferably capable of assembling into a virus-like particle. The term "mutant coat protein" refers to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

Virus-like particle (VLP): VLP as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. In one embodiment, a virus-like particle is a virus particle, in which the viral genome has been physically or chemically inactivated, removed by disassembly and reassembly, or by assembly of purified proteins into a VLP. Typically and more preferably a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA bacteriophage. The term "capsid", refers to a macromolecular assembly composed of viral protein subunits. Typically, there are 60, 120, 180, 240, 300, 360 and more than 360 viral protein subunits. Typically and preferably, the interactions of these subunits lead to the formation of viral capsid with an inherent repetitive organization, wherein said structure typically and preferably is spherical. For example, the capsids of RNA bacteriophages have a spherical form of icosahedral symmetry.

Virus-like particle of an RNA bacteriophage: As used herein, the term "virus-like particle of a RNA bacteriophage" refers to a virus-like particle comprising, or preferably consisting essentially of or consisting of coat proteins, mutants or fragments thereof, of a RNA bacteriophage. In addition, virus-like particle of a RNA bacteriophage resembling the structure of a RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. Preferred VLPs derived from RNA bacteriophages exhibit icosahedral symmetry and consist of 180 subunits. In the context of the invention the term virus-like particle of an RNA bacteriophage preferably relates to a macromolecular structure obtained by the self-assembly of recombinant coat protein of an RNA bacteriophage, or fragments or mutants thereof, wherein preferably said self-assembly took place in the presence of oligonucleotide and aggregated oligonucleotides, respectively.

Agent capable of preventing the self assembly of coat protein: An agent capable of preventing the self assembly of coat protein is an agent which prevents the spontaneous formation of virus-like particles in said mixture. The artisan is able to determine the chemical nature and the appropriate concentration of said agent experimentally, e.g. by analyzing said mixture by size exclusion chromatography, as for example disclosed in Example 9 of WO2007/144150. An agent is capable of preventing the self assembly of coat protein, when after incubation of said mixture for at least 1 h at room temperature, preferably at 22° C., no virus-like particle is detectable by the size exclusion chromatography, as for example disclosed in Example 9 of WO2007/144150. However, agent which is capable of preventing the self assembly of coat protein, does not irreversibly modify said coat protein and removing said agent from said mixture will result in the spontaneous formation of virus-like particles. Preferred agents capable of preventing the self assembly of coat protein comprise detergents, guanidinium hydrochloride and urea, most preferably urea. Preferred detergents are sodium dodecyl sulfate, Tween 20, TritonX 100 and the like. Typically and preferably agents capable of preventing the self assembly of coat protein further comprise a reducing agent such as typically and preferably DDT which keeps intermolecular disulfide bounds formed by cysteine residues of said coat protein in a reduced state.

Purity: The purity of a composition of the invention comprising (i) a virus-like particle, wherein said virus-like particle is a virus-like particle of an RNA bacteriophage, and (ii) aggregated oligonucleotides, wherein said aggregated oligonucleotides are packaged into said virus-like particle, is determined by analytic size exclusion HPLC, wherein said HPLC is performed under conditions essentially, preferably exactly as disclosed in Example 4. The purity of said composition is determined as the percentage of the peak area of said virus-like particle contained in said composition relative to the total peak area of all peaks of the same chromatogram.

One", "a/an": When the terms "one," "a," or "an" are used in this disclosure, they mean "at least one" or "one or more," unless otherwise indicated.

About: within the meaning of the present application the expression about shall have the meaning of +/−4%, typically and preferably of +/−2%. For example about 100 shall mean 96 to 104, typically and preferably 98 to 102.

The present invention provides for a process for producing a nucleotide composition comprising aggregated oligonucleotides said process comprising the steps of: (a) providing oligonucleotides, wherein said oligonucleotides comprise at least one poly G stretch; (b) denaturing said oligonucleotides, wherein said denaturing comprises the step of (i) incubating an aqueous solution I comprising said oligonucleotides and a chaotropic agent at a temperature I until the average diameter of said oligonucleotides is 1 nm or less, wherein preferably said average diameter is determined by Dynamic Light Scattering (DLS), and wherein said temperature I is 75° C. to 99° C., and wherein preferably said chaotropic agent is urea; (c) aggregating said oligonucleotides, wherein said aggregating comprises the steps of (i) incubating an aqueous solution II comprising said oligonucleotides having said average diameter of 1 nm or less obtained in step (b), a chaotropic agent and a cation at a temperature II to form said aggregated oligonucleotides, wherein said incubating is performed until the average diameter of said formed aggregated oligonucleotides is 6-16 nm, wherein preferably said average diameter is determined by Dynamic Light Scattering (DLS), and wherein said temperature II is 75° C. to 99° C., and wherein preferably said chaotropic agent is urea; (ii) adjusting the temperature of said solution II to a temperature III, wherein said temperature III is below 40° C., preferably below 30° C.; wherein said steps are preferably performed in the given order.

The present invention further provides a process for producing aggregated oligonucleotides, wherein said process comprises the steps of: (a) providing oligonucleotides, wherein said oligonucleotides comprise at least one poly G stretch; (b) denaturing said oligonucleotides, wherein said denaturing comprises the step of (i) incubating an aqueous solution I comprising said oligonucleotides and a chaotropic agent at a temperature I until the average diameter of said oligonucleotides is 1 nm or less, wherein preferably said average diameter is determined by Dynamic Light Scattering (DLS), and wherein said temperature I is 75° C. to 99° C., and wherein preferably said chaotropic agent is urea; (c) aggregating said oligonucleotides, wherein said aggregating comprises the steps of (i) incubating an aqueous solution II comprising said oligonucleotides having said average diameter of 1 nm or less obtained in step (b), a chaotropic agent and a cation at a temperature II to form said aggregated oligonucleotides, wherein said incubating is performed until the average diameter of said formed aggregated oligonucleotides is 6-16 nm, wherein preferably said average diameter is determined by Dynamic Light Scattering (DLS), and wherein said temperature II is 75° C. to 99° C., and wherein preferably said chaotropic agent is urea; (ii) adjusting the temperature of said solution II to a temperature III, wherein said temperature III is below 40° C., preferably below 30° C.; wherein said steps are preferably performed in the given order.

In a preferred embodiment, said denaturing said oligonucleotides comprises the step of solubilizing said oligonucleotides in an aqueous solution comprising said chaotropic agent to form said aqueous solution I, wherein said aqueous solution does not comprise mono or divalent ions in a concentration higher than 1 mM, and wherein preferably said aqueous solution does not comprise mono or divalent ions in a concentration higher than 500 µM, preferably not higher than 250 µM, preferably not higher than 100 µM, preferably not higher than 50 µM, preferably not higher than 10 µM.

In a further preferred embodiment, said denaturing said oligonucleotides comprises the step of solubilizing said oligonucleotides in an aqueous solution comprising said chaotropic agent to form said aqueous solution I, wherein said aqueous solution does not comprise mono or divalent ions in a concentration which after the addition of the oligonucleotide would cause said oligonucleotides self-aggregate.

In a further preferred embodiment, said aqueous solution I does not comprise mono or divalent ions in a concentration such that said oligonucleotides self-aggregate.

In a further preferred embodiment, said denaturing said oligonucleotides comprises the step of solubilizing said oligonucleotides in an aqueous solution comprising said chaotropic agent to form said aqueous solution I, wherein said aqueous solution does not comprise mono or divalent ions in a concentration which after the addition of the oligonucleotide would cause said oligonucleotides spontaneously self-aggregate.

In a further preferred embodiment, said aqueous solution I does not comprise mono or divalent ions in a concentration such that said oligonucleotides spontaneously self-aggregate.

In a further preferred embodiment, said denaturing said oligonucleotides comprises the step of solubilizing said oligonucleotides and said chaotropic agent to form said aqueous solution I, and adjusting the temperature of said solution I to temperature I.

In a further preferred embodiment, said chaotropic agent comprised in said solution I is selected from urea, phenol, isopropyl alcohol, ethanol and guanidinium chloride.

In a further preferred embodiment, said chaotropic agent comprised in said solution I is urea.

In a further preferred embodiment, said temperature I is 75° C. to 90° C., preferably 80° C. to 90° C., further preferably 83° C. to 87° C., again further preferably about 85° C., and most preferably 85° C.

In a further preferred embodiment, said incubating said oligonucleotide in said solution I at said temperature I is performed for 10 to 120 min, preferably for 20 to 60 min, further preferably for 20 to 30 min, and again further preferably for 15-18 min.

In a further preferred embodiment, said concentration of said chaotropic agent, preferably said urea, in said solution I is 200 nM to 5M, preferably 500 mM to 2M, further preferably 500 mM to 1.5M, and again further preferably 1M.

In a further preferred embodiment, said concentration of said oligonucleotides, preferably said oligonucleotides of SEQ ID NO:1, in said solution I is 100 µM to 1 mM, preferably 100 µM to 750 µM, further preferably 200 µM to 600 µM, and again further preferably 350 µM to 500 µM.

In a further preferred embodiment, said incubating said oligonucleotides in said solution I at said temperature I is performed between 15 minutes and 120 minutes, preferably between 15 min to 60 min, and further preferably between 15 min to 30 min, again further preferably between 15 min to 25 min.

In a further preferred embodiment, said oligonucleotides comprise at its 5' end at least 3 and at most 15 guanosine entities and at its 3' end at least 3 and at most 15 guanosine entities, preferably at least 6 and at most 13 guanosine entities and at its 3' end at least 6 and at most 13 guanosine entities, further preferably at least 8 and at most 11 guanosine entities and at its 3' end at least 8 and at most 11 guanosine entities.

In a further preferred embodiment, said oligonucleotides comprise a palindromic sequence, wherein preferably said palindromic sequence is GACGATCGTC (SEQ ID NO:2), and wherein further preferably said palindromic sequence is flanked at its 5' end by at least 3 and at most 15 guanosine entities and wherein said palindromic sequence is flanked at its 3' end by at least 3 and at most 15 guanosine entities, and wherein again further preferably said palindromic sequence is flanked at its 5' end by at least 6 and at most 13 guanosine entities and wherein said palindromic sequence is flanked at its 3' end by at least 6 and at most 13 guanosine entities, and wherein again further preferably said palindromic sequence is flanked at its 5' end by at least 8 and at most 11 guanosine entities and wherein said palindromic sequence is flanked at its 3' end by at least 8 and at most 11 guanosine entities.

In a further preferred embodiment, said oligonucleotides comprises 10 to 1000 nucleotides, preferably 10 to 200 nucleotides, further preferably 10 to 100 nucleotides, still further preferably 20 to 40 nucleotides, and still further preferably 30 nucleotides.

In a further preferred embodiment, said oligonucleotides comprise the nucleic acid sequence selected from the group consisting of:
(a) G10: GGGGGGGGGGGGAC-GATCGTCGGGGGGGGGG (SEQ ID NO: 1);
(b) G10-11: GGGGGGGGGGGAC-GATCGTCGGGGGGGGGG (SEQ ID NO: 3);
(c) G12-11: GGGGGGGGGGGGGGAC-GATCGTCGGGGGGGGGGG (SEQ ID NO:4)
(d) G6: GGGGGGGACGATCGTCGGGGGG (SEQ ID NO:5);
(e) G7: GGGGGGGGACGATCGTCGGGGGGG (SEQ ID NO:6);
(f) G8: GGGGGGGGGACGATCGTCGGGGGGGG (SEQ ID NO:7);
(g) G9: GGGGGGGGGGACGATCGTCGGGGGGGGG (SEQ ID NO: 8);
(h) G11: GGGGGGGGGGGGAC-GATCGTCGGGGGGGGGGG (SEQ ID NO: 9)
(i) G6-10: GGGGGGGACGATCGTCGGGGGGGGGG (SEQ ID NO:24);
(j) G7-10: GGGGGGGGAC-GATCGTCGGGGGGGGGG (SEQ ID NO:25);
(k) G8-10: GGGGGGGGGAC-GATCGTCGGGGGGGGGG (SEQ ID NO:26); and
(l) G9-10: GGGGGGGGGGAC-GATCGTCGGGGGGGGGG (SEQ ID NO:27).

In a further preferred embodiment, said oligonucleotides have the nucleic acid sequence G10 GGGGGGGGGGGGAC-GATCGTCGGGGGGGGGG (SEQ ID NO:1).

In a further preferred embodiment, said oligonucleotides exclusively consists of phosphodiester connected deoxynucleotides.

In a further preferred embodiment, the purity of said oligonucleotides, preferably the purity of said oligonucleotides of SEQ ID NO:1, is 90% or higher, as determined by HPLC, preferably by reverse phase HPLC or anion Exchange HPLC, more preferably by reverse phase HPLC.

In a further preferred embodiment, the purity of said oligonucleotides, preferably the purity of said oligonucleotides of SEQ ID NO:1, is 92% or higher, preferably 94% or higher, further preferably 95% or higher, again further preferably 97% or higher, again further preferably 98% or higher, again further preferably 99% or higher, as determined by HPLC, preferably by reverse phase HPLC or anion Exchange HPLC, more preferably by reverse phase HPLC.

In a further preferred embodiment, said oligonucleotides comprise the sequence of SEQ ID NO:1, wherein said oligonucleotides exclusively consists of phosphodiester connected deoxynucleotides.

In a further preferred embodiment, said oligonucleotides consists of the sequence of SEQ ID NO:1.

In a further preferred embodiment, said oligonucleotides consists of the sequence of SEQ ID NO:1, wherein said oligonucleotides exclusively consists of phosphodiester connected deoxynucleotides.

In a further preferred embodiment, said chaotropic agent comprised in said solution II is selected from urea, phenol, isopropyl alcohol, ethanol and guanidinium chloride.

In a further preferred embodiment, said chaotropic agent comprised in said solution II is urea.

Thus, in a further preferred embodiment, said chaotropic agent comprised in said solution II, i.e. in said solution for aggregation, is urea.

In a further preferred embodiment, said temperature II is 75° C. to 90° C., preferably 80° C. to 90° C., further preferably 83° C. to 87° C., again further preferably about 85° C., and most preferably 85° C.

In a further preferred embodiment, said concentration of said chaotropic agent, preferably said urea, in said solution II is 200 nM to 5M, preferably 500 mM to 2M, further preferably 500 mM to 1.5M, and again further preferably 1M.

In a further preferred embodiment, said cation is selected from $Na^+$, $K^+$, $NH_4^+$, $Li^+$, $Ca^{2+}$, $Mg^{2+}$ and $Zn^{2+}$.

Said cation is typically and preferably provided by way of an inorganic salt, and wherein further preferably said inorganic salt are selected from chlorides and sulfates. Preferably, said $Na^+$, $K^+$, $NH_4^+$, $Li^+$, $Ca^{2+}$, $Mg^{2+}$, $Zn^{2+}$ as said cation are provided by its chloride salt. Alternatively, said $Na^+$, $K^+$, $NH_4^+$, $Li^+$, $Ca^{2+}$, $Mg^{2+}$, $Zn^{2+}$ as said cation are provided by its sulfate salt. Again further preferably, said $Na^+$, $K^+$, $NH_4^+$, $Li^+$, $Ca^{2+}$, $Mg^{2+}$ as said cation are provided by its chloride salt, wherein said $Zn^{2+}$ as said cation is preferably provided as its sulfate salt.

In a further preferred embodiment, said the concentration of said cation in said solution II is 20 mM to 2M, preferably 50 mM to 1M, further preferably 100 mM to 500 mM, and again further preferably 250 mM.

In a further preferred embodiment, said chaotropic agent comprised in said solution I and said chaotropic agent comprised in said solution II is the same.

In a further preferred embodiment, the concentration of said chaotropic agent comprised in said solution I and said chaotropic agent comprised in said solution II is the same.

In a further preferred embodiment, said chaotropic agent comprised in said solution I and said chaotropic agent comprised in said solution II is urea.

In a further preferred embodiment, said aggregating said oligonucleotides comprises the steps of (i) solubilizing said chaotropic agent and said cation to form an aqueous solution IIa, (ii) mixing said aqueous solution IIa and said aqueous solution I comprising said oligonucleotides having said average diameter of 1 nm or less obtained in step (b) to form said aqueous solution II, and (iii) adjusting the temperature of said solution II to temperature IT.

In a further preferred embodiment, the difference of temperature of said temperature I and said temperature II is 5° C. or less, preferably 4° C. or less, further preferably 3° C. or less, again further preferably 2° C. or less, again further preferably 1° C. or less, and most preferably said temperature I and said temperature II are equal.

In a further preferred embodiment, said incubating is performed until the average diameter of said aggregated oligonucleotides is 7-14 nm, wherein said average diameter is determined by Dynamic Light Scattering (DLS).

In a further preferred embodiment, said incubating is performed until the average diameter of said aggregated oligonucleotides is 8-14 nm, wherein said average diameter is determined by Dynamic Light Scattering (DLS).

In a further preferred embodiment, said incubating is performed until the average diameter of said aggregated oligonucleotides is 9-14 nm, wherein said average diameter is determined by Dynamic Light Scattering (DLS).

In a further preferred embodiment, said incubating is performed until the average diameter of said aggregated oligonucleotides is 10-14 nm, wherein said average diameter is determined by Dynamic Light Scattering (DLS).

In a further preferred embodiment, said incubating is performed until the average diameter of said aggregated oligonucleotides is 11-13 nm, wherein said average diameter is determined by Dynamic Light Scattering (DLS).

In a further preferred embodiment, said incubating is performed until the average diameter of said aggregated oligonucleotides is 11, 12 or 13 nm, wherein average said diameter is determined by Dynamic Light Scattering (DLS).

In a further preferred embodiment, said incubating is performed until the average diameter of said aggregated oligonucleotides is 12 nm, wherein said average diameter is determined by Dynamic Light Scattering (DLS).

The determination of the average diameter by Dynamic Light Scattering (DLS) in accordance with the present invention, be it that of said oligonucleotides in the course of the denaturing, or be it that of said aggregated oligonucleotides in the course of the aggregation, is highly beneficial since said determinations can be easily effected while the process is running.

This further ensures a very high precision and very high control of the desired size of the oligonucleotides and aggregated oligonucleotides, respectively.

In a further preferred embodiment, said incubating is performed until said aggregated oligonucleotides comprise a relative peak start time of 80 to 110%, where said relative peak start time is determined by size exclusion HPLC with the capsid of an RNA bacteriophage as the standard.

In a further preferred embodiment, said process further comprises the step of purifying said aggregated oligonucleotides, and wherein preferably said purifying comprises filtering said aggregated oligonucleotides, preferably said solution II comprising said aggregated oligonucleotides, through a 50 nm filter.

In a further preferred embodiment, said 50 nm filter is a 50 nm PTFE filter.

In a further preferred embodiment, said filtering said aggregated oligonucleotides, preferably said solution II comprising said aggregated oligonucleotides, through said 50 nm filter, preferably said 50 nm PTFE filter, is performed at 0° C.-20° C.

Said further preferred step of purifying, preferably filtering, allows to remove any large aggregates prior to the packaging step into the VLPs and, thus, further leads typically to an even further increase in purity of the final product, i.e. the inventive VLPs packaged with the aggregated oligonucleotides by typically around 5%. The increase in purity is, thus, typically associated with a decrease in higher molecular weight material in the final product as evidenced by SEC HLPC or DLS.

In a further preferred embodiment, said process does not comprise a step of purifying said aggregated oligonucleotides.

In a further preferred embodiment, said aggregated oligonucleotides comprise at its 5' end at least 3 and at most 15 guanosine entities and at its 3' end at least 3 and at most 15 guanosine entities, preferably at least 6 and at most 13 guanosine entities and at its 3' end at least 6 and at most 13 guanosine entities, further preferably at least 8 and at most 11 guanosine entities and at its 3' end at least 8 and at most 11 guanosine entities.

In a further preferred embodiment, said aggregated oligonucleotides comprise a palindromic sequence, wherein preferably said palindromic sequence is GACGATCGTC (SEQ ID NO:2), and wherein further preferably said palindromic sequence is flanked at its 5' end by at least 3 and at most 15 guanosine entities and wherein said palindromic sequence is flanked at its 3' end by at least 3 and at most 15 guanosine entities, and wherein again further preferably said palindromic sequence is flanked at its 5' end by at least 6 and at most 13 guanosine entities and wherein said palindromic sequence is flanked at its 3' end by at least 6 and at most 13 guanosine entities, and wherein again further preferably said palindromic sequence is flanked at its 5' end by at least 8 and at most 11 guanosine entities and wherein said palindromic sequence is flanked at its 3' end by at least 8 and at most 11 guanosine entities.

In a further preferred embodiment, said aggregated oligonucleotides comprises 10 to 1000 nucleotides, preferably 10 to 200 nucleotides, further preferably 10 to 100 nucleotides, still further preferably 20 to 40 nucleotides, and still further preferably 30 nucleotides.

In a further preferred embodiment, said aggregated oligonucleotides comprise a nucleic acid sequence selected from the group consisting of:
 (a) G10: GGGGGGGGGGGGACGATCGTCGGGGGGGGGG (SEQ ID NO: 1);
 (b) G10-11: GGGGGGGGGGGACGATCGTCGGGGGGGGGGG (SEQ ID NO:3);
 (c) G12-11: GGGGGGGGGGGGGACGATCGTCGGGGGGGGGGG (SEQ ID NO:4)
 (d) G6: GGGGGGGACGATCGTCGGGGGG (SEQ ID NO:5);
 (e) G7: GGGGGGGACGATCGTCGGGGGGG (SEQ ID NO: 6);
 (f) G8: GGGGGGGGGACGATCGTCGGGGGGGG (SEQ ID NO:7);
 (g) G9: GGGGGGGGGACGATCGTCGGGGGGGGG (SEQ ID NO: 8);
 (h) G11: GGGGGGGGGGGGACGATCGTCGGGGGGGGGGG (SEQ ID NO: 9)
 (i) G6-10: GGGGGGGACGATCGTCGGGGGGGGGG (SEQ ID NO:24);
 (j) G7-10: GGGGGGGGACGATCGTCGGGGGGGGGG (SEQ ID NO:25);
 (k) G8-10: GGGGGGGGGACGATCGTCGGGGGGGGGG (SEQ ID NO:26); and
 (l) G9-10: GGGGGGGGGGACGATCGTCGGGGGGGGGG (SEQ ID NO:27).

In a further preferred embodiment, said aggregated oligonucleotides have the nucleic acid sequence GGGGGGGGGGGGACGATCGTCGGGGGGGGGG (SEQ ID NO:1) (G10).

In a further preferred embodiment, said aggregated oligonucleotides exclusively consists of phosphodiester connected deoxynucleotides.

In a further aspect, the present invention provides for a nucleotide composition comprising aggregated oligonucleotides, wherein said nucleotide composition is obtainable by the process for producing a nucleotide composition comprising aggregated oligonucleotides in accordance with the present invention, wherein preferably said aggregated oligonucleotides have an average diameter of 6-16 nm, preferably 7-14 nm, wherein said average diameter is determined by Dynamic Light Scattering (DLS).

In a preferred embodiment, said aggregated oligonucleotides have an average diameter of 8-14 nm, preferably 9-14 nm, further preferably 10-14 nm, wherein said average diameter is determined by Dynamic Light Scattering (DLS).

In a further preferred embodiment, said aggregated oligonucleotides have an average diameter of 11-13 nm, preferably 11, 12 or 13 nm, further preferably 12 nm, wherein said average diameter is determined by Dynamic Light Scattering (DLS).

In a further preferred embodiment, at least 90%, preferably at least 95%, of said aggregated oligonucleotides have a diameter of 10.8 nm to 13.2 nm, wherein said diameter is determined by Dynamic Light Scattering (DLS).

In a further preferred embodiment, said at least 65%, preferably at least 70% of said aggregated oligonucleotides have a diameter of 11.4 nm to 12.6 nm, wherein said diameter is determined by Dynamic Light Scattering (DLS).

In a further preferred embodiment of said nucleotide composition, at least 90%, preferably at least 95%, of said aggregated oligonucleotides have a diameter of 12 nm±10%, i.e. have a diameter of 10.8 nm to 13.2 nm, wherein said diameter is determined by Dynamic Light Scattering (DLS).

In a further preferred embodiment of said nucleotide composition, wherein at least 65%, preferably at least 70% of said aggregated oligonucleotides have a diameter of 12 nm±5%, i.e. have a diameter of 11.4 nm to 12.6 nm, wherein said diameter is determined by Dynamic Light Scattering (DLS).

In a further preferred embodiment, said aggregated oligonucleotides have the nucleic acid sequence G10 GGGGGGGGGGGGACGATCGTCGGGGGGGGGG (SEQ ID NO:1).

In a further preferred embodiment, said aggregated oligonucleotides have the nucleic acid sequence G10 GGGGGGGGGGGGACGATCGTCGGGGGGGGGG (SEQ ID NO:1), and wherein said aggregated oligonucleotides exclusively consists of phosphodiester connected deoxynucleotides.

In an again further aspect, the present invention provides for a nucleotide composition comprising aggregated oligonucleotides, wherein said aggregated oligonucleotides have an average diameter of 7-14 nm, wherein said average diameter is determined by Dynamic Light Scattering (DLS).

In a preferred embodiment, said aggregated oligonucleotides have an average diameter of 8-14 nm, preferably 9-14 nm, further preferably 10-14 nm, wherein said average diameter is determined by Dynamic Light Scattering (DLS).

In a further preferred embodiment, said aggregated oligonucleotides have an average diameter of 11-13 nm, preferably 11, 12 or 13 nm, further preferably 12 nm, wherein said average diameter is determined by Dynamic Light Scattering (DLS).

In a further preferred embodiment, wherein at least 90%, preferably at least 95%, of said aggregated oligonucleotides have a diameter of 10.8 nm to 13.2 nm, wherein said diameter is determined by Dynamic Light Scattering (DLS).

In a further preferred embodiment, wherein at least 65%, preferably at least 70% of said aggregated oligonucleotides have a diameter of 11.4 nm to 12.6 nm, wherein said diameter is determined by Dynamic Light Scattering (DLS).

In a further preferred embodiment of said nucleotide composition, at least 90%, preferably at least 95%, of said aggregated oligonucleotides have a diameter of 12 nm±10%, i.e. have a diameter of 10.8 nm to 13.2 nm, wherein said diameter is determined by Dynamic Light Scattering (DLS).

In a further preferred embodiment of said nucleotide composition, wherein at least 65%, preferably at least 70% of said aggregated oligonucleotides have a diameter of 12 nm±5%, i.e. have a diameter of 11.4 nm to 12.6 nm, wherein said diameter is determined by Dynamic Light Scattering (DLS).

In a further preferred embodiment, said aggregated oligonucleotides have the nucleic acid sequence G10 GGGGGGGGGGGGACGATCGTCGGGGGGGGGG (SEQ ID NO:1).

In a further preferred embodiment, said aggregated oligonucleotides have the nucleic acid sequence G10 GGGGGGGGGGGGACGATCGTCGGGGGGGGGG (SEQ ID NO:1), and wherein said aggregated oligonucleotides exclusively consists of phosphodiester connected deoxynucleotides.

In a further aspect, the present invention provides for a process for producing a composition comprising (i) a virus-like particle, wherein said virus-like particle is a virus-like particle of an RNA bacteriophage, and (ii) aggregated oligonucleotides, wherein said aggregated oligonucleotides are packaged into said virus-like particle, said process comprising the steps of: (a) generating a mixture, wherein said mixture comprises: (i) a coat protein of said RNA bacteriophage; (ii) an agent capable of preventing the self-assembly of said coat protein; and (iii) aggregated oligonucleotides, wherein said aggregated oligonucleotides comprise oligonucleotides comprising at least one poly G stretch, and wherein said aggregated oligonucleotides have an average diameter of 6-16 nm, wherein preferably said average diameter is determined by Dynamic Light Scattering (DLS); (b) removing said agent from said mixture; and (c) allowing said coat protein to self-assemble into a virus-like particle and to package said aggregated oligonucleotides.

In an again further aspect, the present invention provides for a process for producing a composition comprising (i) a virus-like particle, wherein said virus-like particle is a virus-like particle of an RNA bacteriophage, and (ii) aggregated oligonucleotides, wherein said aggregated oligonucleotides are packaged into said virus-like particle, said process comprising the steps of: (a) generating a mixture, wherein said mixture comprises: (i) a coat protein of said RNA bacteriophage; (ii) an agent capable of preventing the self-assembly of said coat protein; and (iii) aggregated oligonucleotides, wherein said aggregated oligonucleotides comprise oligonucleotides comprising at least one poly G stretch, and wherein said aggregated oligonucleotides are obtainable by the process according to the first aspect of the present invention, and wherein said aggregated oligonucleotides have an average diameter of 6-16 nm, wherein preferably said average diameter is determined by Dynamic Light Scattering (DLS); (b) removing said agent from said mixture; and (c) allowing said coat protein to self-assemble into a virus-like particle and to package said aggregated oligonucleotides.

In an again further aspect, the present invention provides for a process for producing a composition comprising (i) a virus-like particle, wherein said virus-like particle is a virus-like particle of an RNA bacteriophage, and (ii) aggregated oligonucleotides, wherein said aggregated oligonucleotides are packaged into said virus-like particle, said process comprising the steps of: (a) generating a mixture, wherein said mixture comprises: (i) a coat protein of said RNA bacteriophage; (ii) an agent capable of preventing the self-assembly of said coat protein; and (iii) the nucleotide composition, wherein said nucleotide composition is obtainable by the process for producing a nucleotide composition comprising aggregated oligonucleotides in accordance with the present invention, and wherein said nucleotide composition comprises said aggregated oligonucleotides, wherein said aggregated oligonucleotides comprise oligonucleotides comprising at least one poly G stretch, and wherein said aggregated oligonucleotides have an average diameter of 6-16 nm, wherein preferably said average diameter is determined by Dynamic Light Scattering (DLS); (b) removing said agent from said mixture; and (c) allowing said coat protein to self-assemble into a virus-like particle and to package said aggregated oligonucleotides.

During said processes said virus-like particle is formed by self-assembly of coat protein of said RNA bacteriophage in the presence of said aggregated oligonucleotides.

In a preferred embodiment, said aggregated oligonucleotides have an average diameter of 8-14 nm, preferably 9-14 nm, further preferably 10-14 nm, wherein said average diameter is determined by Dynamic Light Scattering (DLS).

In a further preferred embodiment, said aggregated oligonucleotides have an average diameter of 11-13 nm, preferably 11, 12 or 13 nm, further preferably 12 nm, wherein said average diameter is determined by Dynamic Light Scattering (DLS).

In a further preferred embodiment, said coat protein comprises recombinant proteins, or fragments thereof, that are capable of self-assembly, of a RNA bacteriophage.

In a further preferred embodiment, said coat protein consists of recombinant proteins, or fragments thereof, that are capable of self-assembly, of a RNA bacteriophage.

In a further preferred embodiment, said RNA bacteriophage is selected from the group consisting of:
  (a) bacteriophage Qβ;
  (b) bacteriophage R17;
  (c) bacteriophage fr;
  (d) bacteriophage GA;
  (d) bacteriophage SP;
  (e) bacteriophage MS2;
  (f) bacteriophage M11;
  (g) bacteriophage MX1;
  (h) bacteriophage NL95;
  (i) bacteriophage f2;
  (j) bacteriophage PP7; and
  (k) bacteriophage AP205.

In a further preferred embodiment, said RNA bacteriophage is Qβ.

In a further preferred embodiment, said coat protein comprises a sequence selected from the group consisting of:
(a) SEQ ID NO:10 (Qβ CP);
(b) a mixture of SEQ ID NO:10 and SEQ ID NO:11 (Qβ A1 protein);
(c) SEQ ID NO: 12 (R17 coat protein);
(d) SEQ ID NO: 13 (fr coat protein);
(e) SEQ ID NO: 14 (GA coat protein);
(f) SEQ ID NO: 15 (SP coat protein);
(g) a mixture of SEQ ID NO: 15 and SEQ ID NO: 16;
(h) SEQ ID NO:17 (MS2 coat protein);
(i) SEQ ID NO:18 (M11 coat protein);
(j) SEQ ID NO:19 (MXI coat protein);
(k) SEQ ID NO:20 (NL95 coat protein);
(l) SEQ ID NO:21 (f2 coat protein);
(m) SEQ ID NO:22 (PP7 coat protein); and
(n) SEQ ID NO:23 (AP205 coat protein).

In a further preferred embodiment, said coat protein comprises the sequence of SEQ ID NO:10 (Qβ CP).

In a further preferred embodiment, said coat protein comprises a mixture of SEQ ID NO:10 and SEQ ID NO:11 (Qβ A1 protein).

In a further preferred embodiment, said coat protein consist of the sequence of SEQ ID NO:10 (Qβ CP).

In a further preferred embodiment, said coat protein consists of a mixture of SEQ ID NO:10 and SEQ ID NO:11 (Qβ A1 protein).

In a further preferred embodiment, the concentration of said coat protein in said mixture is 1 to 4 mg/ml, preferably 2.5 mg/ml.

In a further preferred embodiment, the concentration of said aggregated oligonucleotides in said mixture is 25 to 100 μM, preferably 62.5 μM.

In a further preferred embodiment, said the molar ratio of said aggregated oligonucleotides and said coat protein in said mixture is 0.5 to 1.2, preferably 0.7.

In a further preferred embodiment, said agent comprises a denaturing compound selected from urea and guanidinium hydrochloride.

In a further preferred embodiment, said agent comprises a denaturing compound, wherein said denaturing compound is urea, and wherein preferably the concentration of said urea in said mixture is 0.25 to 7.2 M, preferably 1 M.

In a further preferred embodiment, said agent further comprises a reducing agent.

In a further preferred embodiment, said reducing agent is DTT, wherein preferably the concentration of said DTT in said mixture is 1 to 25 mM, preferably 2.5 mM.

In a further preferred embodiment, said removing of said agent from said mixture is performed by a first buffer exchange with a first buffer, wherein said first buffer comprises sodium chloride, and wherein preferably the concentration of said sodium chloride in said first buffer is 50 to 350 mM, preferably 250 mM.

In a further preferred embodiment, said first buffer exchange is performed across a membrane, wherein said membrane comprises a molecular weight cut off of 1 to 50 kD, preferably of 5 to 30 kD, most preferably of 30 kD.

In a further preferred embodiment, said process further comprises the step of contacting said virus-like particle with an oxidizing agent, wherein preferably said oxidizing agent is selected from the group consisting of
(a) hydrogen peroxide, wherein preferably the concentration of said hydrogen peroxide is 0.25-50 mM, preferably 2 mM;
(b) oxygen;
(c) gluthathion;
(d) $Cu^{2+}$; and
(e) $Fe^{3+}$.

In a further preferred embodiment, said oxygen as oxidizing agent can be sterile filtered air, typically and preferably sterile filtered ambient air.

In a further preferred embodiment, said process further comprises the step of purifying said virus-like particle, and wherein said purifying comprises a second buffer exchange with a second buffer, wherein said second buffer is a pharmaceutically acceptable buffer.

In a further preferred embodiment, said second buffer exchange is performed using a membrane, wherein said membrane comprises a molecular weight cut off of 50 to 1000 kD.

In a further preferred embodiment, said second buffer exchange is performed using a membrane, wherein said membrane comprises a molecular weight cut off of 100 to 300 kD.

In a further preferred embodiment, said the purity of said composition is at least 99.5%, preferably at least 99.6%, more preferably at least 99.7%, still more preferably at least 99.8%, and most preferably at least 99.9% as determined by size exclusion chromatography.

In an again further aspect, the present invention provides for a composition comprising (i) a virus-like particle of an RNA bacteriophage, and (ii) aggregated oligonucleotides, wherein said aggregated oligonucleotides are packaged into said virus-like particle, wherein said composition is obtainable by a process for producing a composition comprising (i) a virus-like particle, wherein said virus-like particle is a virus-like particle of an RNA bacteriophage, and (ii) aggregated oligonucleotides in accordance with the present invention.

In an again further aspect, the present invention provides for a composition comprising (i) a virus-like particle of an RNA bacteriophage, and (ii) aggregated oligonucleotides, wherein said aggregated oligonucleotides are packaged into said virus-like particle, wherein said aggregated oligonucleotides have an average diameter of 6-16, preferably of 7-14 nm, wherein said average diameter is determined by Dynamic Light Scattering (DLS).

In a further preferred embodiment, said RNA bacteriophage is bacteriophage Q.

In a further preferred embodiment, said virus-like particle of RNA bacteriophage Qβ consists of coat proteins comprising the sequence of SEQ ID NO:10 (Qβ CP).

In a further preferred embodiment, said virus-like particle of RNA bacteriophage Qβ consists of coat proteins comprising a mixture of SEQ ID NO:10 and SEQ ID NO:11 (Qβ A1 protein).

In a further preferred embodiment, said virus-like particle of RNA bacteriophage Qβ consists of coat proteins consisting of the sequence of SEQ ID NO:10 (Qβ CP).

In a further preferred embodiment, said virus-like particle of RNA bacteriophage Qβ consists of coat proteins consisting of a mixture of SEQ ID NO:10 and SEQ ID NO:11 (Qβ A1 protein).

In a further preferred embodiment, said aggregated oligonucleotides have the nucleic acid sequence G10 GGGGGGGGGG GACGATCGTC GGGGGGGGGG (SEQ ID NO:1).

In a further preferred embodiment, said aggregated oligonucleotides have the nucleic acid sequence G10 GGGGGGGGGGGGACGATCGTCGGGGGGGGGG (SEQ ID NO:1), and wherein said aggregated oligonucleotides exclusively consists of phosphodiester connected deoxynucleotides.

In a further preferred embodiment, the purity of said composition is at least 99.5%, preferably at least 99.6%, more preferably at least 99.7%, still more preferably at least 99.8%, and most preferably at least 99.9% as determined by size exclusion chromatography.

In a further preferred embodiment, said aggregated oligonucleotides have an average diameter of 6-16, preferably of 7-14 nm, wherein said average diameter is determined by Dynamic Light Scattering (DLS).

In a further preferred embodiment, said aggregated oligonucleotides have an average diameter of 8-14 nm, preferably 9-14 nm, further preferably 10-14 nm, wherein said average diameter is determined by Dynamic Light Scattering (DLS).

In a further preferred embodiment, said aggregated oligonucleotides have an average diameter of 11-13 nm, preferably 11, 12 or 13 nm, further preferably 12 nm, wherein said average diameter is determined by Dynamic Light Scattering (DLS).

In a further preferred embodiment, wherein at least 90%, preferably at least 95%, of said aggregated oligonucleotides have a diameter of 10.8 nm to 13.2 nm, wherein said diameter is determined by Dynamic Light Scattering (DLS).

In a further preferred embodiment, wherein at least 65%, preferably at least 70% of said aggregated oligonucleotides have a diameter of 11.4 nm to 12.6 nm, wherein said diameter is determined by Dynamic Light Scattering (DLS).

In a further preferred embodiment of said composition, at least 90%, preferably at least 95%, of said aggregated oligonucleotides have a diameter of 12 nm±10%, i.e. have a diameter of 10.8 nm to 13.2 nm, wherein said diameter is determined by Dynamic Light Scattering (DLS).

In a further preferred embodiment of said composition, wherein at least 65%, preferably at least 70% of said aggregated oligonucleotides have a diameter of 12 nm±5%, i.e. have a diameter of 11.4 nm to 12.6 nm, wherein said diameter is determined by Dynamic Light Scattering (DLS).

EXAMPLES

The Examples are intended to illustrate the present invention without restricting it. In the Examples described below, unless otherwise indicated, all temperatures are set forth in degrees Celsius (° C.). Reagents were purchased from commercial suppliers such as Sigma Aldrich, Boston Bioproducts, Invitrogen, Alfa Aesar or the like, and were used without further purification unless otherwise indicated. The water used in the described reactions has been purified or treated to remove all contaminants and salts. The removal of inorganic ionic impurities is confirmed by measuring the conductivity of the water. Water used in this application has a resistivity of typically and preferably at least 18 MΩ·cm at 25° C. This ensures residual inorganic impurities such as salts are less than 1 ppb.

The purity of the oligonucleotides, in particular, of the oligonucleotide G10 of SEQ ID NO:1, was determined by ion-pair, reversed-phase high performance liquid chromatography (IP-RP-HPLC) or by anion exchange—high performance liquid chromatography (IEX-HPLC).

IP-RP-HPLC was effected using a Waters Xbridge BEH C18 4.6×75 mm, 2.5 μm column at a column temperature of 70±2° C., a flow rate of 0.4 mL/min, a wavelength of 260 nm, an injection volume of 5 μL and a run time of 40 minutes.

IEX-HPLC was effected using a Dionex DNAPac PA200 4.0×250 mm part #063000 column at a column temperature of 30±2° C., a flow rate of 1.0 mL/min, a wavelength of 260 nm, an injection volume of 20 μL and a run time of 45 minutes.

IP-RP-HPL.C//G10: Samples are injected on a oligonucleotide ion pairing column and elution is carried out using a combined water acetonitrile gradient modified with TEA and HFIP as the ion pairing buffer with detection at 260 nm. The resulting oligonucleotide G10 peak is integrated separately from the remaining peaks consisting of oligonucleotide G10 subpopulations such as G10+1n, G10-1n, G10-2n, G10-3n, >G10+1n and <G10-3n (whereby n=deoxynucleotide).

IEX-HPLC//G10: Samples are injected on a strong anion-exchange column and analyzed under denaturing conditions (pH≥10). Elution is carried out using a combined salt and methanol gradient with detection at 260 nm. The resulting oligonucleotide G10 peak is integrated separately from the remaining peaks consisting of oligonucleotide G10 subpopulations such as G10+1n, G10-1n, G10-2n, G10-3n, >G10+1n and <G10-3n (whereby n=deoxynucleotide).

Example 1

Denaturation and Aggregation of Oligonucleotide G10 (SEQ ID NO:1)

Quantification of G10: Oligonucleotide G10 (SEQ ID NO: 1) was quantified by UV absorption at 260 nm corrected by the absorption at 340 nm, wherein 1 A260-340 corresponds to a concentration of 27.8 μg/ml at 1 cm path length.

Denaturation: (10.0 ml scale, 500 μM G10 of a purity of about 94% as determined by reverse phase HPLC and anion Exchange HPLC (referred to as high purity G10 oligonucleotide in this Example section), 1M Urea, 85° C., 20 min): 70.6 mg G10 were weighed into a 15 ml tube. The powder was dissolved in 10.0 ml purified water (with a resistivity at 25° C. of 18.2 MΩ·cm) containing 1M urea (c=500 μM; content of bulk powder determined prior to dilution by spectrometry). The mixture was disaggregated for 20 minutes at 85° C. in a water bath. Aliquots were taken, immediately cooled down in an ice/water bath to 0° C., removed from the ice bath, and allowed to warm to room temperature naturally, and DLS and optionally size exclusion HPLC (SEC) measurements conducted as described in Example 3 and Example 4. The remainder of the sample was held at 85° C. and the aggregation step conducted.

FIG. 1A shows a DLS of the denatured high purity G10 oligonucleotide obtained with the inventive process as a single peak. The measured average diameter of the G10 oligonucleotide of 0.90 nm indicates that denaturing is complete and monomers have been achieved. This fully denatured G10 oligonucleotide ensures and allows the formation a well-controlled and defined aggregated G10 oligonucleotides within the desired range in accordance with the present invention as outlined below.

Aggregation (20.0 ml scale, 250 μM G10 denatured as above, 250 mM Na$^+$Cl$^-$ 20 mM Sodium Phosphate (pH=7.2), 1M urea 85° C., 8-30 min): 10 ml of the denatured 500 μM G10 solution at 85° C. referred above were mixed with a solution of 10 ml of 500 mM NaCl, 40 mM Sodium Phosphate, and 1M urea at 85° C. in a 25 ml tube. The mixture was incubated for 15 minutes at 85° C. in a water bath. The solution was cooled down in an ice/water bath to 0° C. Aliquots were taken therefrom, allowed to warm to room temperature, and DLS and optionally size exclusion HPLC (SEC) measurements conducted. Aggregated oligonucleotide solutions are typically and preferably used within 3 hours if stored <20° C.

A final filtration step can be utilized to remove eventual trace (<1%) of large particles. This is performed by passing the previously cooled, room temperature solution of aggregated oligonucleotides through a 50 nm filter.

Figure 1B:
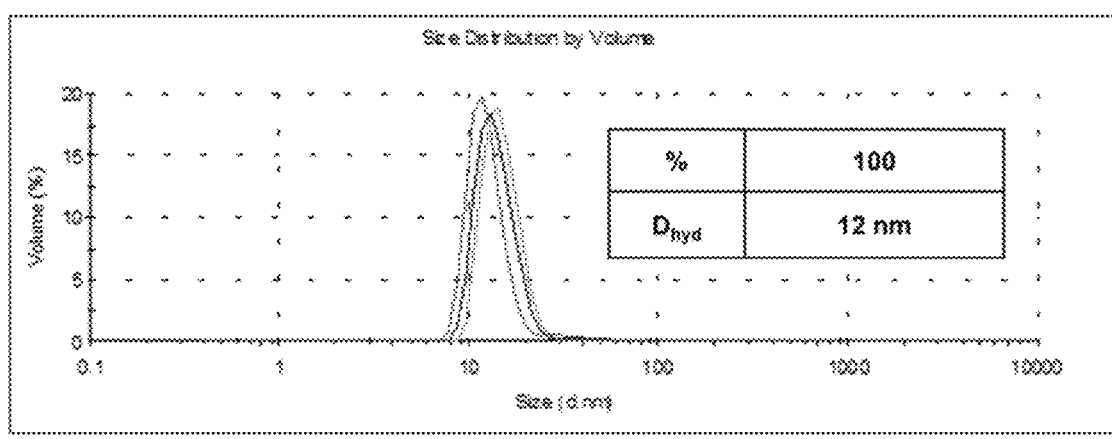
FIG. 1B: Dynamic Light Scattering (DLS) of denatured oligonucleotide G10 and aggregated oligonucleotides G10 as obtained by the inventive process. DLS was performed as described in Example 3.

FIG. 1B shows a DLS of the subsequently aggregated G10 oligonucleotides obtained with the inventive process. The very preferred aggregated G10 oligonucleotides obtained show proper aggregation and an average diameter of 12 nm. These well-controlled and defined aggregated G10 oligonucleotides within the desired preferred range in accordance with the present invention will result in very high purity packaged and well-formed VLPs as outlined below.

The denaturation and aggregation of the very preferred oligonucleotide G10 (SEQ ID NO:1) were further conducted at different oligonucleotide concentrations, wherein basically the same DLS as depicted in FIG. 1A and FIG. 1B were obtained. Thus, denaturation was effected using various concentrations of the oligonucleotide G10 of between 100 μm and 1 mM. The subsequent aggregation step were then effected by exactly half that concentration as used for the denaturation as a matter of convenience due to a 1:1 mixing of the two solutions as described herein.

Example 2

Denaturation and Aggregation of Oligonucleotides G10-11, G12-11, G6, G7, G8, G9, G11, G6-10, G7-10, G8-10, and G9-10 (SEQ ID NOs: 3-9, 24-27)

Denaturation: A solution of 500 μM oligonucleotide G10-11 (SEQ ID NO:3), G12-11 (SEQ ID NO:4), G6 (SEQ ID NO:5), G7 (SEQ ID NO:6), G8 (SEQ ID NO:7), G9 (SEQ ID NO:8), G11 (SEQ ID NO:9), G6-10 (SEQ ID NO:24), G7-10 (SEQ ID NO:25), G8-10 (SEQ ID NO:26) or G9-10 (SEQ ID NO:27) in 1M urea was disaggregated for 20 minutes at 85° C. in a water bath.

Aggregation: (10.0 ml scale, 250 μM G10, 250 mM Na+, 20 mM Sodium Phosphate, 1M urea 85° C., 8-30 min): 5 ml denatured solution of oligonucleotides G10-11 (SEQ ID NO:3), G12-11 (SEQ ID NO:4), G6 (SEQ ID NO:5), G7 (SEQ ID NO:6), G8 (SEQ ID NO:7), G9 (SEQ ID NO:8), G11 (SEQ ID NO:9), G6-10 (SEQ ID NO:24), G7-10 (SEQ ID NO:25), G8-10 (SEQ ID NO:26) or G9-10 (SEQ ID NO:27) at 85° C., 5 ml of 500 mM Na+, 40 mM Sodium Phosphate, and 1M urea at 85° C. were mixed in a 15 ml tube (250 μM oligo, 1 M urea, 20 mM Sodium Phosphate, 250 mM Na+). The mixture was incubated for 15 minutes at 85° C. in a water bath. The solution was cooled down in an ice/water bath to 0° C. Aliquots were taken therefrom, allowed to warm to room temperature, and DLS and optionally size exclusion HPLC (SEC) measurements conducted. Aggregated oligonucleotide solutions are typically and preferably used within 3 hours if stored <20° C.

The products of the aggregation processes were analyzed by Dynamic Light Scattering (DLS) as described in Example 3 and by size exclusion HPLC as described in Example 4. DLS of the aggregated oligonucleotides revealed that the average diameter of all the aggregated oligonucleotides were between 11-13 nm, as determined by Dynamic Light Scattering (DLS), and all within 80%-110% PST, as determined by size exclusion HPLC.

Example 3

Analysis of the Aggregation of Oligonucleotide G10 by Dynamic Light Scattering

The particle size of the oligonucleotides, aggregated oligonucleotides and VLPs packaged with aggregated oligonucleotides in accordance with the present invention was determined using dynamic light scattering (DLS). Instrument settings as used for the present examples and as preferred for determining the particle size of the oligonucleotides, aggregated oligonucleotides and VLPs packaged with aggregated oligonucleotides in accordance with the present invention are presented below.

Instrument: Malvern Zetasizer Nano ZS
Light Source: He—Ne laser (633 nm at 4 mW (maximum))

The middle column of Table 1 represents the settings applied for a reference standard (polystyrene microspheres) and for calibration that confirmed that the instrument was performing properly. The right column represents the settings applied in the method used for our analysis and measurements of the oligonucleotides, aggregated oligonucleotides and VLPs packaged with aggregated oligonucleotides.

TABLE 1

Instrument settings for standard and inventive compositions

| Application: | Reference Standard: polystyrene microspheres | Inventive products, aggregated oligonucleotides, compositions of packaged VLPs |
|---|---|---|
| Type: | Size | Size |
| Material: | Polystyrene Latex | DNA/Protein |
| Refractive Index RI: | 1.59 | 1.45 |
| Absorbance (ABS): | 0.01 | 0 |
| Dispersant: | $H_2O$ | PBS |
| Temperature: | 25° C. | 25° C. |
| Viscosity: | 0.8872 cP | 1.33 cP |
| Refractive Index RI: | 1.33 | 1.33 |
| Equilibration time: | 20 sec | 60 sec |
| Detection angle: | 173° (backscatter) | 173° (backscatter) |
| Run duration: | 10 sec | 30 sec |
| Number of runs per measurement: | 3-5, preferably 3 | 3-5, preferably 3 |

The DLS software calculates average hydrodynamic radii, and through basic multiplication, the particle average diameter is determined. 2× particle average radius=Particle diameter. For consistency, particle size will henceforth be reported and used throughout the present invention as average diameter measured in nanometers ($D_{Hyd}$).

Example 4

Analysis of the Aggregation of Oligonucleotide G10 by Size Exclusion HPLC

The aggregation state of the aggregated G10 oligonucleotides was analyzed essentially as described in WO 2007/144150 by analytical size exclusion HPLC using the following conditions:

Column: TSKgel 5000 PWXL 7.8 mm*30.0 cm (Lot: 5PWX06GNMH3304, Art: 08023, Tosoh Bioscience)
Eluent: PBS (150 mM NaCl in 20 mM sodium phosphate buffer, pH 7.2)
Injection volume: 40.0 μl (preferably comprising a concentration of about 20 μM to about 500 μM)

Flow rate: 0.8 ml/min
Gradient: Isocratic
Run time: 20 min
Wavelength: 215, 260 and 280 nm, data evaluation at 260 nm
Column oven temp.: 25° C.
Autosampler temp.: 8° C.
Capsid of bacteriophage Qβ was used as standard.

The peak start time X % of G10 relative to Qβ capsid (relative peak start time Qβ) was calculated as follows: X %=peak start time [min] of the oligonucleotide divided by the retention time of Qβ capsid standard [min]×100%, wherein the peak start time of the oligonucleotide was determined as the time when the elution of the oligonucleotide became detectable, and wherein the retention time of the Qβ capsid standard was determined as the time of the occurrence of the maximum peak of the standard. An Example of an elution profile of oligonucleotide G10 and capsid of bacteriophage Qβ as standard is depicted in FIG. 1 of WO2007/144150. Based on the chromatograms depicted in FIG. 1 of WO2007/144150 a relative peak start time of 88% was calculated for the aggregated oligonucleotide.

Example 5

Comparison of Denatured Oligonucleotides G10 Obtained by the Inventive Process and by Prior Art Processes The oligonucleotide G10 of SEQ ID NO:1 with two different purities (79% and 94% as determined by reverse phase HPLC and anion Exchange HPLC; referred to as low and high purity G10 oligonucleotide in this Example section) were each subjected to the disaggregation (denaturation) as described in the prior art (WO2007/144150). The same high purity (94%) oligonucleotide G10 was subjected to the denaturation as described in Example 1 herein. The impurities of the used oligonucleotide G10 are mostly "failure sequences" meaning oligonucleotide sequences with lower number of G residues, be it 26 mers, 27 mers, 28 mers and 29 mers.

Figure 2A:
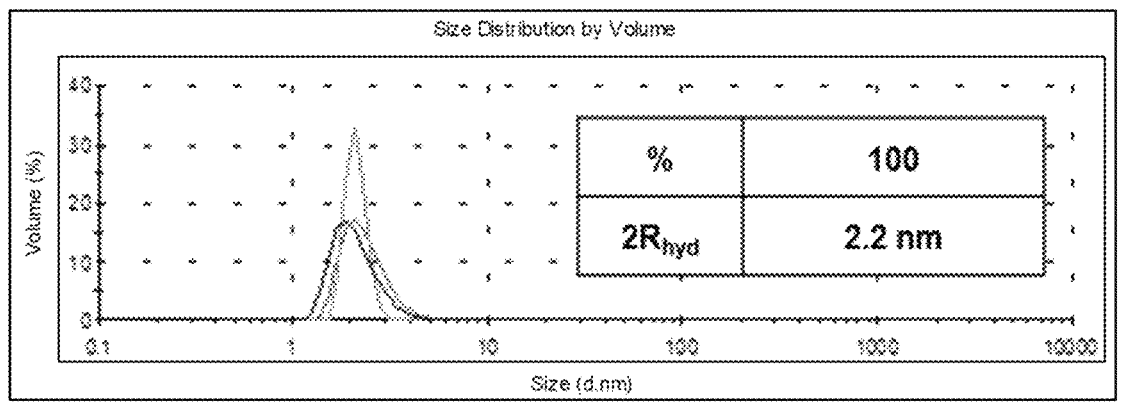
FIG. 2A: DLS of denatured oligonucleotides G10. DLS was performed as described in Example 3. Low purity oligonucleotide G10 of SEQ ID NO:1 (about 79% as determined by reverse phase HPLC and anion Exchange HPLC) was used for the disaggregation (denaturation) as described in the prior art (WO2007/144150). DLS shows particles with an average diameter of 2.2 nm indicating that not all oligonucleotide G10 secondary structure has been disrupted and denatured to monomer. Multiple scans were performed as shown by the overlapping curves. The average diameter ($D_{hyd}$) and percent of primary peak (mean) of these scans are reported within data box inset in the graph.
Figure 2B:
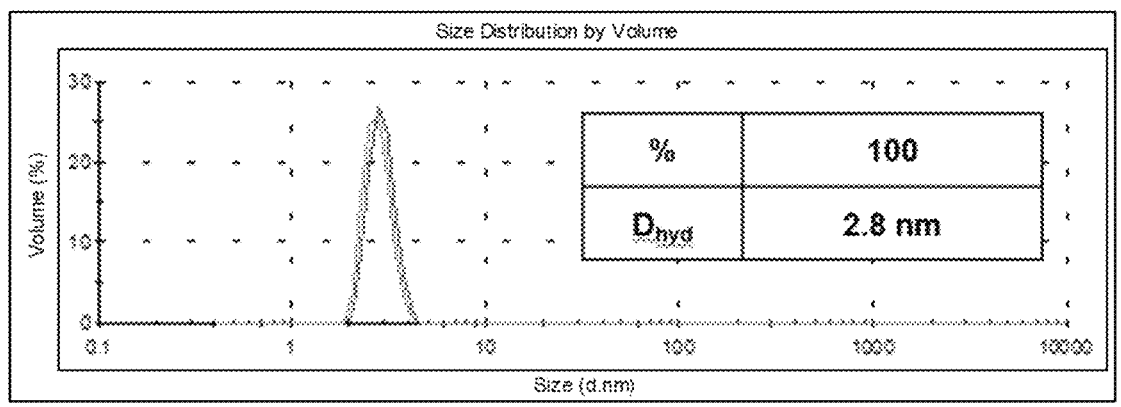
FIG. 2B: DLS of denatured oligonucleotides G10. DLS was performed as described in Example 3. High purity oligonucleotide G10 of SEQ ID NO:1 (about 94% as determined by reverse phase HPLC and anion Exchange HPLC) was used for the disaggregation (denaturation) as described in the prior art (WO2007/144150). DLS shows particles with an average diameter of 2.8 nm indicating that not all oligonucleotide G10 secondary structure has been disrupted and denatured to monomer. Multiple scans were performed as shown by the overlapping curves. The average diameter ($D_{hyd}$) and percent of primary peak (mean) of these scans are reported within data box inset in the graph.
Figure 2C:
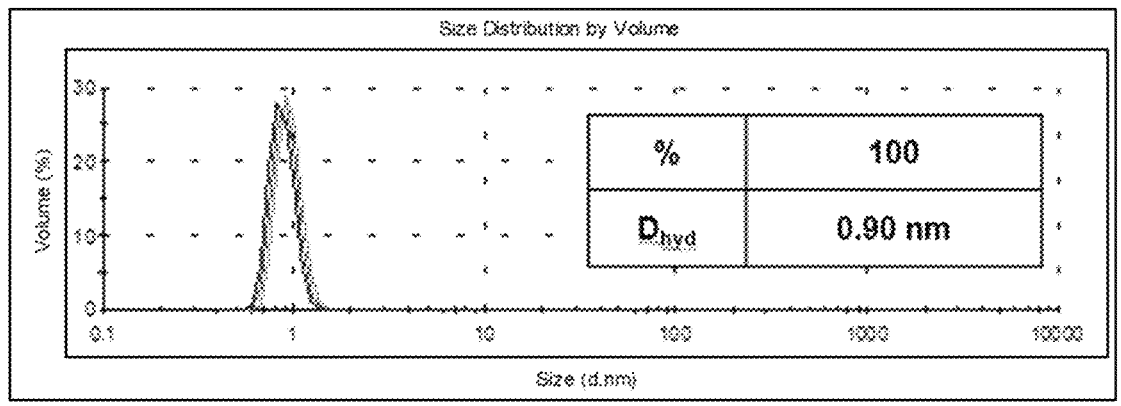
FIG. 2C: DLS of denatured oligonucleotides G10. DLS was performed as described in Example 3. High purity oligonucleotide G10 of SEQ ID NO:1 (about 94% as determined by reverse phase HPLC and anion Exchange HPLC) was used for the denaturation of the inventive process. DLS shows particles with an average diameter of 0.9 nm indicating that oligonucleotide G10 has been completely or substantially completely denatured to monomer. Multiple scans were performed as shown by the overlapping curves. The average diameter ($D_{hyd}$) and percent of primary peak (mean) of these scans are reported within data box inset in the graph.

The resulting products were analyzed by DLS as described in Example 3 and are shown in FIG. 2A (Low purity G10, prior art process) and FIG. 2B (High purity G10, prior art process) and FIG. 2C (High purity G10, inventive process). The completely denatured oligonucleotide G10 monomer has a hydrodynamic average diameter of approximately 1 nm.

The low purity G10 subjected to the denaturing prior art process resulted in particles with an average diameter of 2.2 nm indicating the presence of secondary structures and that not all oligonucleotide G10 has been completely denatured to monomer (FIG. 2A). The high purity G10 subjected to the denaturing prior art process resulted in particles with an average diameter of 2.8 nm indicating the presence of secondary structures and that not all oligonucleotide G10 has been completely denatured to monomer (FIG. 2B). As will be discussed in Example 6, this incomplete denaturing will lead to more variable, and further to larger, aggregated oligonucleotides.

The high purity G10 subjected to the denaturing of the inventive process resulted in particles with an average diameter of 0.9 nm indicating that oligonucleotide G10 has been completely or substantially completely denatured to monomer (FIG. 2C). As indicated, this fully denatured G10 oligonucleotide ensures and allows the formation of well-controlled and defined aggregated G10 oligonucleotides within the desired range in accordance with the present invention.

The proper denaturing of the oligonucleotides such as shown for the very preferred oligonucleotide G10 leading to complete, or at least almost complete, denaturing and to monomers prior to the start of the aggregation step is highly preferred and important. If secondary structures exist, dimers, trimers, or quadruplexes of the oligonucleotides, the aggregation step will be more variable, and the final aggregated oligonucleotides will be larger and of a broader size distribution.

Example 6

Comparison of Aggregated Oligonucleotides G10 Obtained by the Inventive Process and by Prior Art Processes The G10 materials obtained from the denaturing experiments as described in Example 5 were subjected to aggregation, either as described in the prior art (WO2007/144150), or as described by the inventive process, and hereby as described in Example 1 above.

Figure 3A:
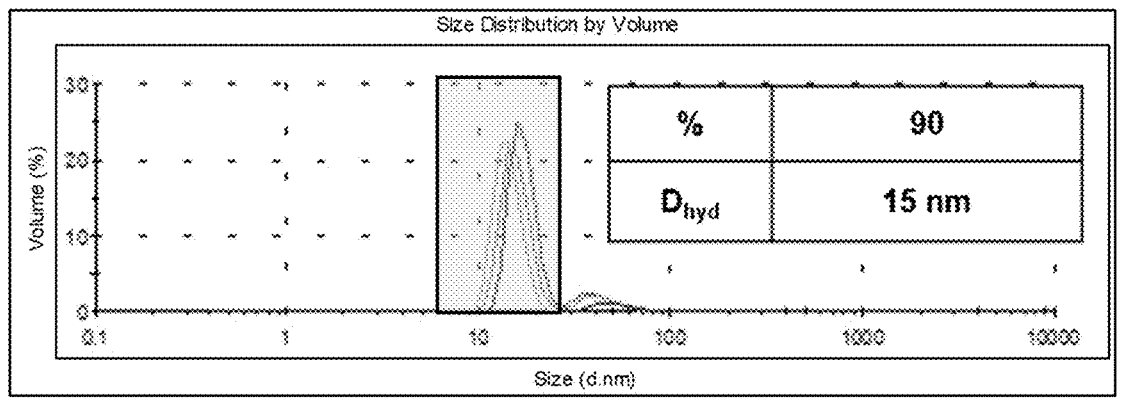
FIG. 3A: DLS of aggregated oligonucleotides G10. DLS was performed as described in Example 3. Denatured oligonucleotides as obtained from Example 5 (FIG. 2A-2C) were used. Aggregation as described in the prior art (WO2007/144150) of low purity G10 denatured by prior art process. Low purity oligonucleotide G10 of SEQ ID NO:1 corresponds to about 79% purity as determined by reverse phase HPLC and anion Exchange HPLC. DLS shows aggregated oligonucleotides which are not only on the high side of the desired particle range (15 nm), but additionally, 10% of the material is significantly larger (30-50 nm). Multiple scans were performed as shown by the overlapping curves. The average diameter ($D_{hyd}$) and percent of primary peak (mean) of these scans are reported within data box inset in the graph.
Figure 3B:
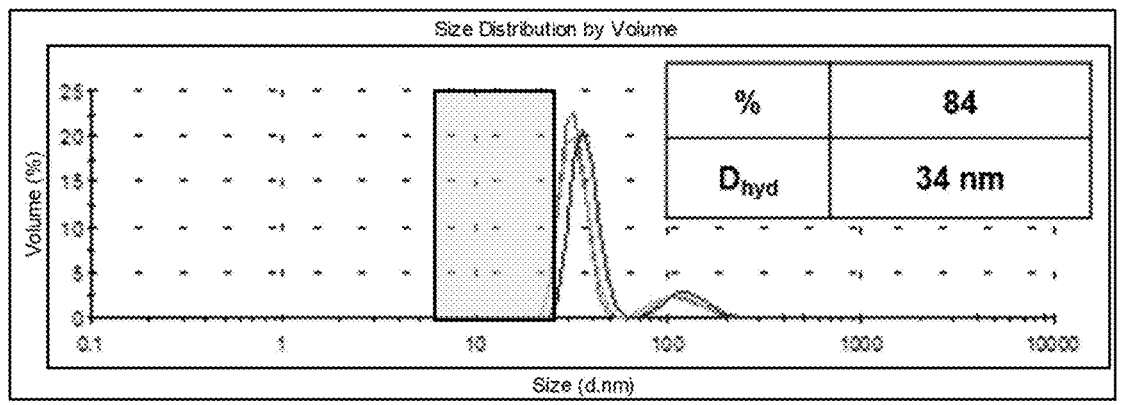
FIG. 3B: DLS of aggregated oligonucleotides G10. DLS was performed as described in Example 3. Denatured oligonucleotides as obtained from Example 5 (FIG. 2A-2C) were used. Aggregation as described in the prior art (WO2007/144150) of high purity G10 denatured by prior art process. High purity oligonucleotide G10 of SEQ ID NO: XX corresponds to about 94% purity as determined by reverse phase HPLC and anion Exchange HPLC. DLS shows aggregated oligonucleotides with an average diameter being completely (100%) outside the diameter range of 6-16 nm (the desired range) as illustrated by the shaded box. Multiple scans were performed as shown by the overlapping curves. The average diameter ($D_{hyd}$) and percent of primary peak (mean) of these scans are reported within data box inset in the graph.
Figure 3C:
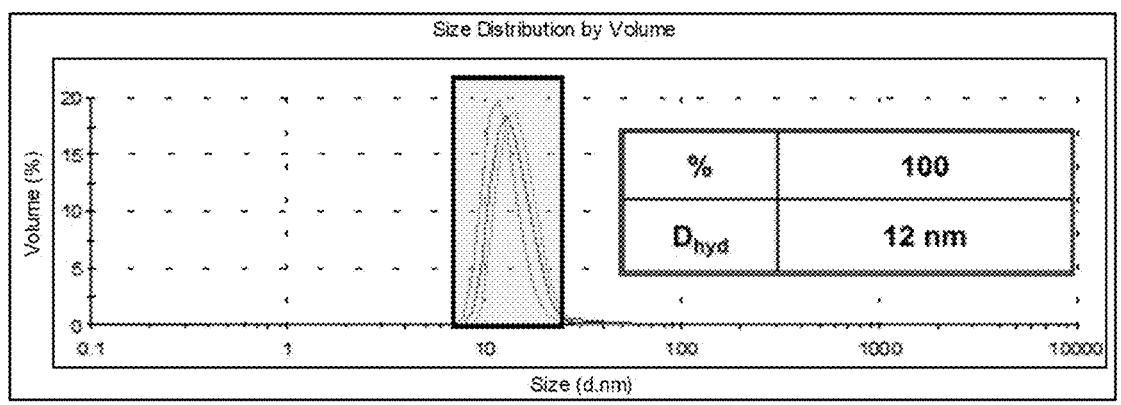
FIG. 3C: DLS of aggregated oligonucleotides G10. DLS was performed as described in Example 3. Denatured oligonucleotides as obtained from Example 5 (FIG. 2A-2C) were used. Aggregation of high purity G10 in accordance with the present inventive process. High purity oligonucleotide G10 of SEQ ID NO:1 corresponds to about 94% purity as determined by reverse phase HPLC and anion Exchange HPLC. DLS shows aggregated oligonucleotides with an average diameter of said aggregated oligonucleotides being completely (100%) within the diameter range of 6-16 nm (the desired range) as illustrated by the shaded box. Multiple scans were performed as shown by the overlapping curves. The average diameter ($D_{hyd}$) and percent of primary peak (mean) of these scans are reported within data box inset in the graph.

The resulting aggregated oligonucleotides were analyzed by DLS as described in Example 3 herein and are shown in FIG. 3A (prior art aggregation of low purity G10 denatured by prior art process) and FIG. 3B (prior art aggregation of high purity G10 denatured by prior art process) and FIG. 3C (inventive aggregation of high purity G10 denatured by inventive process).

The low purity material denatured and aggregated with the prior art process resulted in aggregated oligonucleotides which are not only on the high side of the desired average diameter range (6-16 nm), but additionally, 10% of the material is too large (30-40 nm) for subsequent proper packaging into VLP's of RNA bacteriophages, preferably of RNA bacteriophages Qβ (FIG. 3A). As a result of this larger and wide particle distribution, the final packaged VLPs will be less pure by SEC and DLS and rod like structures will be observed in the electron micrographs (see Example 8 below). It has to be noted that said rod like structures cannot typically be separated by purification via filtration but requires more costly and intense purification via chromatography which is very detrimental for manufacturing at scale, and in particular, for GMP manufacturing.

The high purity material denatured and aggregated with the prior art process resulted in aggregated oligonucleotides all of which are too large for packaging into VLP's of RNA bacteriophages, preferably of RNA bacteriophages Qβ, and, therefore will result in unstable VLPs (FIG. 3B). Additionally, a second peak at ~100 nm is identified. It is noteworthy that optimization of the prior art process using the high purity material by decreasing the time of aggregation was not performed due to the fact that the then required heating and cooling times would be shorter than what could be easily controlled at either the lab or at manufacturing scale. The present inventive processes were, in fact, able to overcome said disadvantage of the prior art processes.

Thus, and to the contrary, the high purity material denatured and aggregated with the process of the present invention resulted in aggregated oligonucleotides having an average diameter of 12 nm indicating proper aggregation (FIG. 3B). This well-controlled and defined aggregated G10 oligonucleotides within the desired very preferred range in accordance with the present invention will result in very high purity and well-formed packaged VLPs.

The proper aggregation of the oligonucleotides such as shown for the very preferred oligonucleotide G10 leading to a complete, or at least almost complete, narrowly defined diameter size distribution is further highly preferred and important. Controlling the aggregation leading to aggregated oligonucleotides of an average diameter of 11-13 nm, preferably of an average diameter of 12 nm, as determined by DLS as described in Example 3 ensures and allows to achieve a high purity packaged VLP.

If the aggregated oligonucleotides are too big, the resulting material after the packaging step will have large impurities as shown in the DLS, and malformed VLPs such as rod like structures as shown in the electron micrographs. If the aggregated oligonucleotides are very large >50 nm, unstable VLPs can result.

Example 7

Packaging of Qβ VLPs with Aggregated Oligonucleotides G10 by Disassembly/Reassembly Disassembly of Qβ VLPs: 45 mg Qβ VLP (2.5 mg/ml, as determined by Bradford analysis) in PBS (20 mM Phosphate, 150 mM NaCl, pH 7.5), was reduced with 10 mM DTT for 15 min at RT under stirring conditions. Then, magnesium chloride was added to 0.7 M final concentration and the incubation was continued for 15 min at RT under stirring conditions, leading to precipitation of the encapsulated host cell RNA and concomitant disintegration of the VLPs. The solution was centrifuged 10 min at 4000 rpm at 4° C. (Eppendorf 5810 R, in fixed angle rotor A-4-62 used in all following steps) in order to remove the precipitated RNA from the solution. The supernatant, containing the released, dimeric Qβ coat protein, was used for the chromatographic purification steps.

In an alternative and preferred manner, the Qbeta capsid was disassembled into Qbeta dimer by the addition of 1 M DTT to a final concentration of 10 mM DTT. Nucleic acid and host cell proteins were precipitated by increasing the NaCl concentration to 600 mM and adjusting the pH to pH 2.6 by the addition of 1 M Sodium Phosphate, 0.75 M Citric Acid. The precipitated nucleic acids and HCP were removed by TFF using a Sartoflow Beta Crossflow system fitted with 2×0.5 m² Millipore Biomax 300 membranes ran using the following operating parameters: $P_{Feed}$=0.9, $P_{Retentate}$=0.4 bar and $P_{Permeate}$=0.2 bar resulting in a TMP of 0.45 bar. The material was diafiltered against 3 DVs of 20 mM Sodium Phosphate, 20 mM Citric acid, 300 mM Sodium Chloride pH 3.3.

Purification of Q coat protein by cation exchange chromatography and size exclusion chromatography: The supernatant of the disassembly reaction, containing dimeric coat protein, host cell proteins and residual host cell RNA, was loaded onto a SP-Sepharose FF column (xk16/20, 6 ml, Amersham Bioscience). The column was equilibrated with 20 mM sodium phosphate buffer pH 7 and the sample was diluted 1:15 in water to adjust a conductivity below 10 mS/cm in order to achieve proper binding of the coat protein to the column. The elution of the bound coat protein was accomplished by a step gradient to 20 mM sodium phosphate/500 mM sodium chloride and the protein was collected in a fraction volume of approx. 25 ml. The chromatography was carried out at RT with a flow rate of 5 ml/min during all steps and the absorbance was monitored at 260 nm and 280° nm. In a second step, the isolated Qβ coat protein (the eluted fraction from the cation exchange column) was loaded onto a Sephacryl S-100 HR column (xk26/60, 320 ml, Amersham Bioscience) equilibrated with 20 mM sodium phosphate/250 mM sodium chloride; pH 7.2. The chromatography was carried out at RT with a flow rate of 2.5 ml/min and the absorbance was monitored at 260 nm and 280 nm. Fractions of 5 ml were collected.

Figure 4:
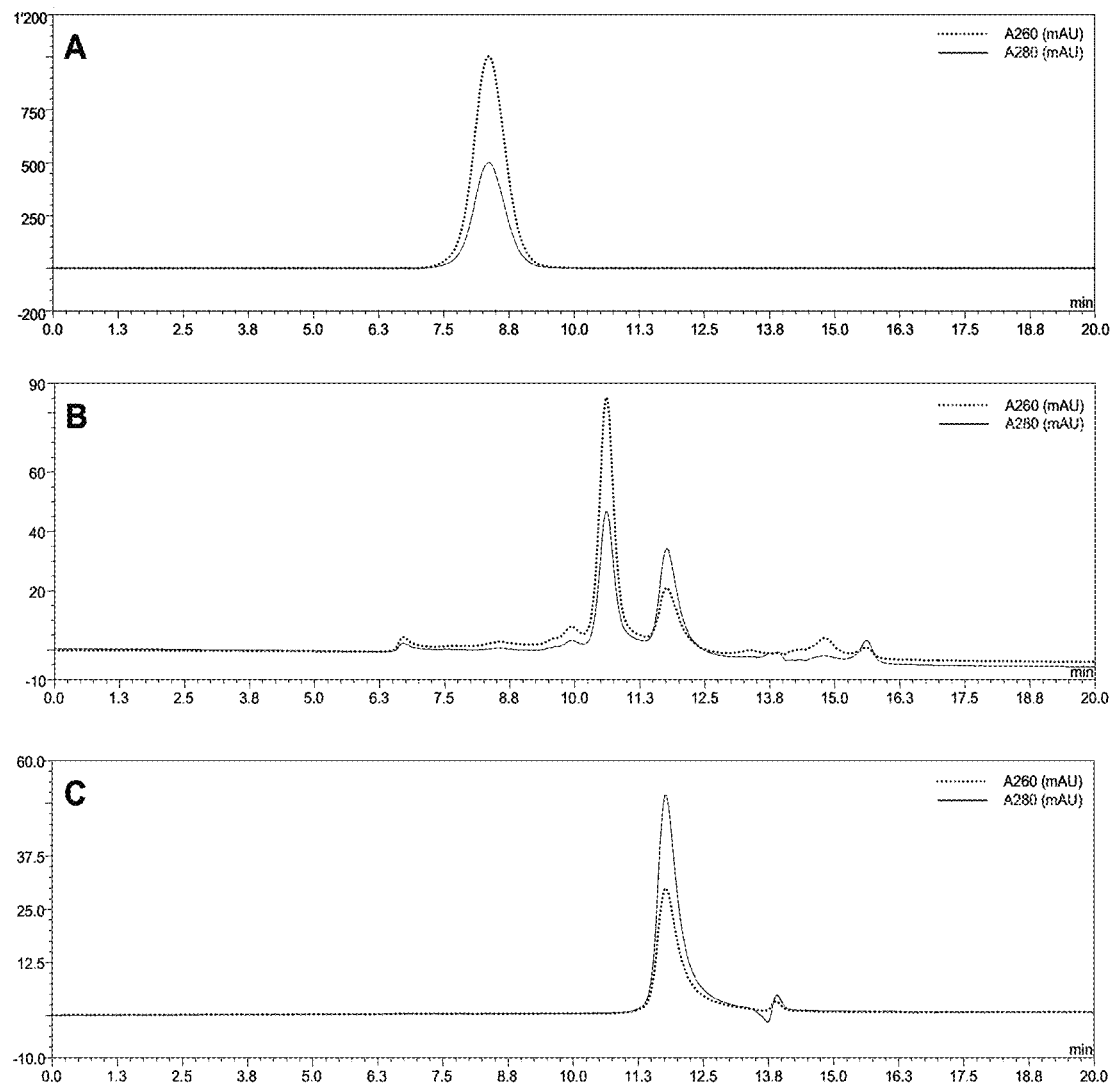
FIG. 4A: Characterization of purified Qβ coat protein by analytical size exclusion chromatography. Sample of purified Qβ VLP. The observed peak (ratio A260/A280=2) is dominated by the RNA core of the VLP, because the absorption coefficient of RNA at 260 nm is approx. 100 fold higher than the absorption coefficient of the coat protein.
FIG. 4B: Characterization of purified Qβ coat protein by analytical size exclusion chromatography. Sample of the supernatant of the disassembly reaction. Released coat protein is indicated by the presence of the protein-like peak at approx. 12 min. Furthermore several species of non-precipitated RNA molecules are present in the range 6.8 to 11 min.
FIG. 4C: Characterization of purified Qβ coat protein by analytical size exclusion chromatography. Sample of purified Qβ coat protein. Analysis was performed in PBS on column TSK G5000PWxl (Tosoh Bioscience).

Characterization of purified Qβ coat protein by analytical size exclusion chromatography: A sample of purified Qβ coat protein was analyzed by analytical size exclusion chromatography (FIG. 4C) and compared to i) intact Qβ VLP (FIG. 4A), which had been purified from *E. coli* lysate and which was used as source material for the purification procedure, and ii) to the supernatant of the disassembly reaction (FIG. 4B). Efficient separation of RNA molecules from the coat protein is indicated by the absence of any RNA-like peak (typical ratio of A280/A260=0.5) in FIG. 4C and the presence of a unique protein-like peak (typical ratio of A280/A260=1.7).

In an alternative and preferred manner, purification of Qβ coat protein were effected by cation exchange chromatography and Mustang Q membrane: CEX Chromatography was performed as a capture step for the Qbeta dimer. SP Sepharose FF resin was packed into a BPG140 column using an AKTA Ready Chromatography system and 150 mM NaCl as the packing buffer. The bed height of the packed column was 14.0 cm, equivalent to a bed volume of 2.2 L. HETP analysis gave an asymmetry factor of 1.55 and a theoretical plate count of 2560 plates per meter. The diafiltrate from the disassembly step was filtered through a Millipore Opticap XL 5 capsule prior to loading. Chromatography was performed using the method shown in Table 2.

TABLE 2

Cation Exchange Chromatography Method

| Step | Buffer | CV |
| --- | --- | --- |
| Sanitisation | 0.5 M NaOH (5 hr contact time) | 5 |
| Equilibration | 20 mM Sodium Phosphate 300 mM NaCl pH 3.3 | 5 |
| Load | CEX Load | Up to 15 g/L |
| Wash 1 | 20 mM Sodium Phosphate, 300 mM NaCl pH 3.3 | 5 |
| Wash 2 | 20 mM Sodium Phosphate, 300 mM NaCl pH 7.2 | 10 |
| Elution | 20 mM Sodium Phosphate, 550 mM NaCl pH 7.2 | 5 |
| High Salt Regeneration | 20 mM Sodium Phosphate, 1150 mM NaCl pH 7.2 | 3 |
| CIP | 0.5 M NaOH (5 hr contact time) | 3 |
| Storage | 20% (v/v) Ethanol, 0.1 M NaCl | 1.5 |

A flow rate 144 cm/h for Sanitisation and Equilibration. 216 cm/h was used for all other steps.

Filtration through a Mustang Q capsule was performed to reduce endotoxin and any residual nucleic acid. The CEX Pool was initially filtered using a 0.2 μm Millipak 60 filter (Cat. No. MPGL06GH2) prior to filtration through a Mustang Q filter at a flow rate of 200 ml/min. The flowthrough collected from the Mustang Q filter was then passed through a second 0.2 μm Millipak 60 filter.

Assembly of QβG10 by diafiltration: Purified coat protein (in 20 mM sodium phosphate pH 7.2, 250 mM NaCl) was mixed with water and stock solutions of urea, NaCl, DTT and aggregated G10 oligonucleotides (prepared as described in Example 1). The volume of the mixture was 50 ml and the final concentrations of the components were 1 mg/ml coat protein, 1.0 M urea, 250 mM NaCl, 2.5 mM DTT and 0.24 mg/ml G10. The solution was then diafiltrated at room temperature against 300 ml of 20 mM sodium phosphate 250 mM NaCl pH 7.2, using a 30 kDa cut off cartridge (Pellicon XL, Millipore) and a cross flow rate of 10 ml/min and a permeate flow rate of 2.5 ml/min. $H_2O_2$ was added to 7 mM final concentration and the solution incubated for 1 h at RT in order to induce the formation of disulfide bonds. The solution was then diafiltrated against 500 ml of 20 mM sodium phosphate 150 mM NaCl pH 7.2, using a 300 kDa cut off cartridge (Pellicon XL, Millipore) and a cross flow rate of 10 ml/min and a permeate flow rate of 2.5 ml/min, in order to remove excess of $H_2O_2$ and non-packaged G10 oligonucleotides from the assembled QβG10 product.

Alternatively, the packaging of Qβ VLPs with the aggregated oligonucleotides G10 as obtained by the present invention can be further be effected as described in Example 10 of WO2007/144150.

Example 8

Comparison of Qβ VLPs Packaged with Aggregated Oligonucleotides G10 as Obtained by the Present Invention and by Prior Art Processes—DLS and EM Qβ VLPs were prepared in analogy to Example 7 described above using not only the aggregated G10 oligonucleotides prepared as described in Example 1, but further using the aggregated G10 oligonucleotides prepared by the prior art processes as described in Example 6 above.

Figure 5A:
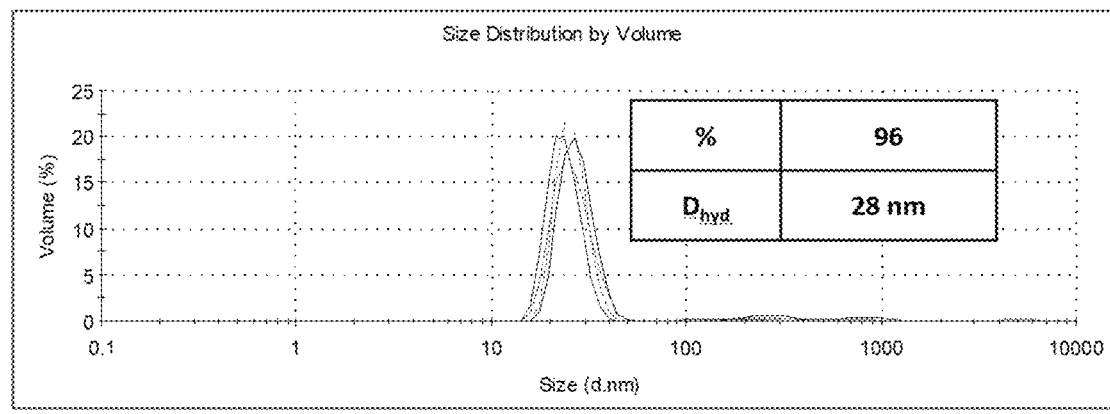
FIG. 5A: DLS and Electron Micrographs (EM) pictures of virus-like particle (VLP) of RNA bacteriophage Qβ packaged with aggregated oligonucleotides G10 obtained by the disaggregation-aggregation method of prior art and by the denaturation and aggregation of the present invention. DLS was performed as described in Example 3 and EM was taken as described in Example 8. DLS of QβVLPs packaged with aggregated oligonucleotides G10 obtained by the disaggregation-aggregation method of the prior art. Multiple scans were performed as shown by the overlapping curves. The average diameter ($D_{hyd}$) and percent of primary peak (mean) of these scans are reported within data box inset in the graph.
Figure 5B:
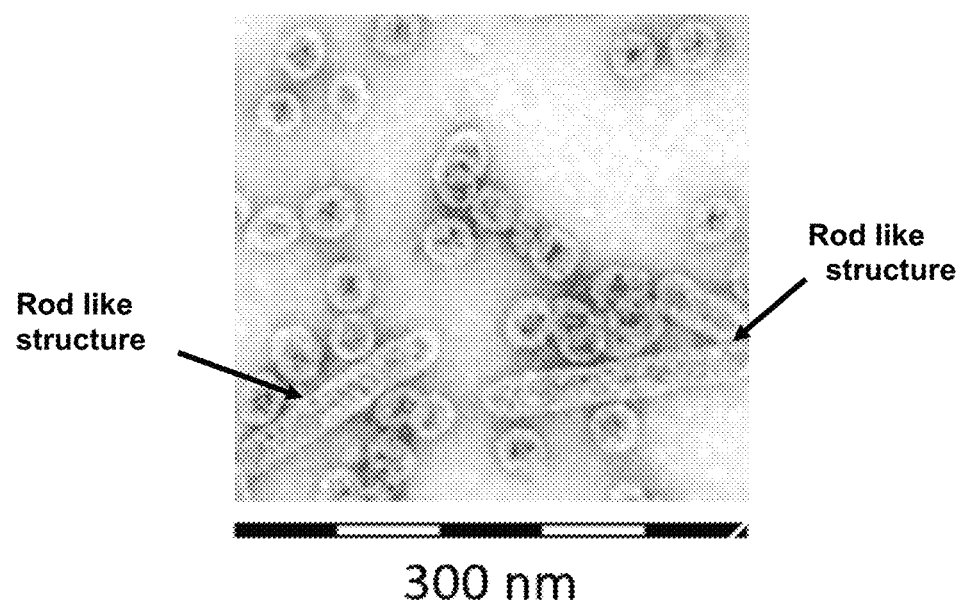
FIG. 5B: DLS and Electron Micrographs (EM) pictures of virus-like particle (VLP) of RNA bacteriophage Qβ packaged with aggregated oligonucleotides G10 obtained by the disaggregation-aggregation method of prior art and by the denaturation and aggregation of the present invention. DLS was performed as described in Example 3 and EM was taken as described in Example 8. EM of QβVLPs packaged with aggregated oligonucleotides G10 obtained by the disaggregation-aggregation method of the prior art. Arrows included to identify the rod like structures.

The aggregated oligonucleotides shown in FIG. 3A, which were obtained by prior art aggregation of low purity G10 denatured by prior art process, and having a wide size distribution with 10% being too large for packaging, when subjected to the packaging step resulted in VLPs having a DLS as shown in FIG. 5A and an EM as shown in FIG. 5B. The DLS revealed a major peak (96%) of an average diameter of 28 nm corresponding to properly formed VLPs (30 nm±2 nm), but additional large particle peaks were observed as well. The corresponding EM shows spherical VLPs with said average diameter, but also rod like structures much larger than the desired 30 nm VLPs.

Figure 5C:
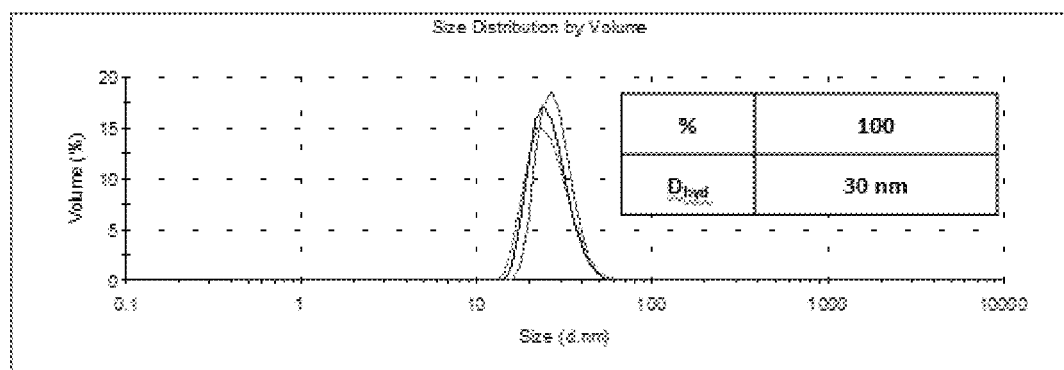
FIG. 5C: DLS and Electron Micrographs (EM) pictures of virus-like particle (VLP) of RNA bacteriophage Qβ packaged with aggregated oligonucleotides G10 obtained by the disaggregation-aggregation method of prior art and by the denaturation and aggregation of the present invention. DLS was performed as described in Example 3 and EM was taken as described in Example 8. DLS of QβVLPs packaged with aggregated oligonucleotides G10 obtained by the inventive process. Multiple scans were performed as shown by the overlapping curves. The average diameter ($D_{hyd}$) and percent of primary peak (mean) of these scans are reported within data box inset in the graph.
Figure 5D:
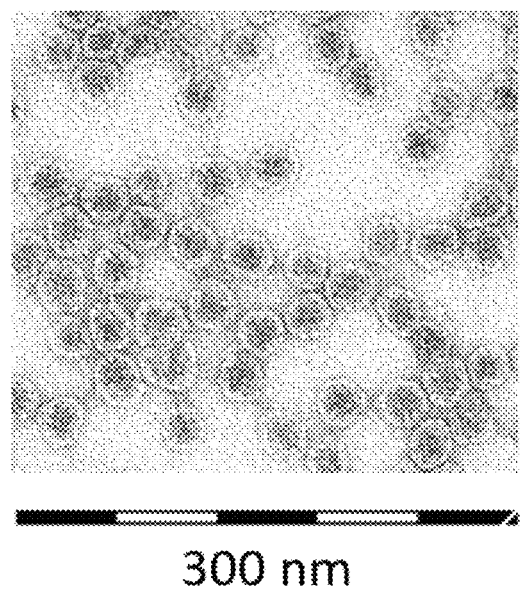
FIG. 5D: DLS and Electron Micrographs (EM) pictures of virus-like particle (VLP) of RNA bacteriophage Qβ packaged with aggregated oligonucleotides G10 obtained by the disaggregation-aggregation method of prior art and by the denaturation and aggregation of the present invention. DLS was performed as described in Example 3 and EM was taken as described in Example 8. EM of QβVLPs packaged with aggregated oligonucleotides G10 obtained by the inventive process.

To the contrary, the high purity material denatured and aggregated with the process of the present invention when subjected to the packaging step resulted in packaged VLP's of one average diameter and purely formed VLPs. The DLS shows one single peak at 30 nm and no large particles (FIG. 5C) and the EM shows all spherical VLPs with no rod like structures (FIG. 5D).

Example 9

Denaturing Step of the Inventive Process Effected with Varied Parameters

The denaturation of oligonucleotide G10 (SEQ ID NO:1) as described in Example 1 was investigated by varying the concentration of urea, denaturing time, and temperature applied for said denaturation. A bulk oligonucleotide G10 solution was obtained by dissolving G10 (high purity of 94%) in water to a concentration of 1 mM. Urea solutions were added to obtain final denaturing solutions of 500 μM G10 with urea concentrations from 0.1M to 1M. Aliquots of these samples were then incubated at a range of temperature between 25° C. and 85° C. for 20 or 60 minutes. Samples were immediately cooled down in an ice/water bath to 0° C., removed from the ice bath, and allowed to warm to room temperature naturally, and DLS measurements as described in Example 3 conducted. Table 3 shows that successful denaturing, i.e. an average diameter of 1 nm or less, can be achieved irrespective of the urea concentration of 0.2 M to 1.0 M.

TABLE 3

Urea Concentration and Temperature Impact on G10 Oligonucleotide Denaturing

| Urea Concentration | Time (min) | Temperature (° C.) | Average Diameter of 1 nm or less |
|---|---|---|---|
| 0.1 M | 60 | 85 | No |
| 0.2 M | 60 | 85 | Yes |
| 0.5 M | 20 | 85 | Yes |
| 1.0 M | 60 | 75 | Yes |
| 1.0 M | 20 | 85 | Yes |
| 1.0 M | 60 | 85 | Yes |

---

The invention claimed is:

1. A process for producing a nucleotide composition comprising aggregated oligonucleotides, said process comprising the steps of:
   (a) providing oligonucleotides which comprise 3 to 15 guanosine entities at the 5' end and 3 to 15 guanosine entities at the 3' end, and wherein said oligonucleotides comprise phosphodiester connected deoxynucleotides;
   (b) denaturing said oligonucleotides, wherein said denaturing comprises the step of
      (i) incubating an aqueous solution I comprising said oligonucleotides and a chaotropic agent at 75° C. to 99° C. until the average diameter of said oligonucleotides is 1 nm or less, wherein said average diameter is determined by Dynamic Light Scattering (DLS),
   (c) aggregating said oligonucleotides, wherein said aggregating comprises the steps of
      (i) incubating an aqueous solution II comprising said oligonucleotides having said average diameter of 1 nm or less obtained in step (b), a chaotropic agent and a cation at 75° C. to 99° C. to form said aggregated oligonucleotides, wherein said incubating is performed until the average diameter of said formed aggregated oligonucleotides is 7-14 nm, wherein said average diameter is determined by Dynamic Light Scattering (DLS),
      (ii) adjusting the temperature of said solution II to below 40° C.

2. The process of claim 1, wherein said aqueous solution I does not comprise mono or divalent ions in a concentration such that said oligonucleotides spontaneously self-aggregate.

3. The process of claim 1, wherein said chaotropic agent comprised in said solution I is selected from urea, phenol, isopropyl alcohol, ethanol and guanidinium chloride.

4. The process of claim 1, wherein said oligonucleotides comprises 10 to 100 nucleotides.

5. The process of claim 1, wherein said oligonucleotides comprise the nucleic acid sequence selected from the group consisting of:

(a) G10: GGGGGGGGGGGAC-GATCGTCGGGGGGGGGG (SEQ ID NO:1);
   (b) G10-11: GGGGGGGGGGGAC-GATCGTCGGGGGGGGGGG (SEQ ID NO:3);
   (c) G12-11: GGGGGGGGGGGGGAC-GATCGTCGGGGGGGGGGG (SEQ ID NO:4)
   (d) G6: GGGGGGGACGATCGTCGGGGGG (SEQ ID NO:5);
   (e) G7: GGGGGGGGACGATCGTCGGGGGGG (SEQ ID NO:6);
   (f) G8: GGGGGGGGGACGATCGTCGGGGGGGG (SEQ ID NO:7);
   (g) G9: GGGGGGGGGGACGATCGTCGGGGGGGGG (SEQ ID NO:8);
   (h) G11: GGGGGGGGGGGGAC-GATCGTCGGGGGGGGGGG (SEQ ID NO:9)
   (i) G6-10: GGGGGGGACGATCGTCGGGGGGGGGG (SEQ ID NO:24);
   (j) G7-10: GGGGGGGGAC-GATCGTCGGGGGGGGGG (SEQ ID NO:25);
   (k) G8-10: GGGGGGGGGAC-GATCGTCGGGGGGGGGG (SEQ ID NO:26); and
   (l) G9-10: GGGGGGGGGGAC-GATCGTCGGGGGGGGGG (SEQ ID NO:27).

6. The process of claim 1, wherein the purity of said oligonucleotides is 90% or higher, as determined by HPLC.

7. The process of claim 1, wherein said chaotropic agent comprised in said solution II is selected from urea, phenol, isopropyl alcohol, ethanol and guanidinium chloride.

8. The process of claim 1, wherein said chaotropic agent comprised in said solution I and said chaotropic agent comprised in said solution II is urea.

9. The process of claim 1, wherein said incubating is performed until the average diameter of said aggregated oligonucleotides is 9-14 nm, wherein said average diameter is determined by Dynamic Light Scattering (DLS).

10. The process of claim 1, wherein said oligonucleotides have the nucleic acid sequence GGGGGGGGGGGAC-GATCGTCGGGGGGGGGG (SEQ ID NO:1) (G10).

* * * * *

SEQUENCE LISTING

<160> NUMBER OF SEQ ID NOS: 27

<210> SEQ ID NO 1
<211> LENGTH: 30
<212> TYPE: DNA
<213> ORGANISM: artificial sequence
<220> FEATURE:
<223> OTHER INFORMATION: chemically synthesized

<400> SEQUENCE: 1
gggggggggg gacgatcgtc gggggggggg           30

<210> SEQ ID NO 2
<211> LENGTH: 10
<212> TYPE: DNA

```
<213> ORGANISM: artificial sequence
<220> FEATURE:
<223> OTHER INFORMATION: chemically synthesized

<400> SEQUENCE: 2
gacgatcgtc                                                              10

<210> SEQ ID NO 3
<211> LENGTH: 31
<212> TYPE: DNA
<213> ORGANISM: artificial sequence
<220> FEATURE:
<223> OTHER INFORMATION: chemically synthesized

<400> SEQUENCE: 3
gggggggggg gacgatcgtc gggggggggg g                                      31

<210> SEQ ID NO 4
<211> LENGTH: 33
<212> TYPE: DNA
<213> ORGANISM: artificial sequence
<220> FEATURE:
<223> OTHER INFORMATION: chemically synthesized

<400> SEQUENCE: 4
gggggggggg gggacgatcg tcgggggggg ggg                                    33

<210> SEQ ID NO 5
<211> LENGTH: 22
<212> TYPE: DNA
<213> ORGANISM: artificial sequence
<220> FEATURE:
<223> OTHER INFORMATION: chemically synthesized

<400> SEQUENCE: 5
gggggggacg atcgtcgggg gg                                                22

<210> SEQ ID NO 6
<211> LENGTH: 24
<212> TYPE: DNA
<213> ORGANISM: artificial sequence
<220> FEATURE:
<223> OTHER INFORMATION: chemically synthesized

<400> SEQUENCE: 6
ggggggggac gatcgtcggg gggg                                              24

<210> SEQ ID NO 7
<211> LENGTH: 26
<212> TYPE: DNA
<213> ORGANISM: artificial sequence
<220> FEATURE:
<223> OTHER INFORMATION: chemically synthesized

<400> SEQUENCE: 7
ggggggggga cgatcgtcgg gggggg                                            26

<210> SEQ ID NO 8
<211> LENGTH: 28
<212> TYPE: DNA
<213> ORGANISM: artificial sequence
<220> FEATURE:
<223> OTHER INFORMATION: chemically synthesized

<400> SEQUENCE: 8
gggggggggg acgatcgtcg gggggggg                                          28
```

<210> SEQ ID NO 9
<211> LENGTH: 32
<212> TYPE: DNA
<213> ORGANISM: artificial sequence
<220> FEATURE:
<223> OTHER INFORMATION: chemically synthesized

<400> SEQUENCE: 9
gggggggggg ggacgatcgt cggggggggg gg        32

<210> SEQ ID NO 10
<211> LENGTH: 132
<212> TYPE: PRT
<213> ORGANISM: bacteriophage Qb

<400> SEQUENCE: 10

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 11
<211> LENGTH: 329
<212> TYPE: PRT
<213> ORGANISM: bacteriophage Qb

<400> SEQUENCE: 11

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

-continued

```
Leu Asn Pro Ala Tyr Trp Thr Leu Leu Ile Ala Gly Gly Ser Gly
    130                 135                 140

Ser Lys Pro Asp Pro Val Ile Pro Asp Pro Pro Ile Asp Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
                180                 185                 190

Val Glu Leu Gln Pro Arg Glu Phe Asp Val Ala Leu Lys Asp Leu Leu
                195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
                260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325
```

```
<210> SEQ ID NO 12
<211> LENGTH: 129
<212> TYPE: PRT
<213> ORGANISM: bacteriophage R17

<400> SEQUENCE: 12

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr
```

```
<210> SEQ ID NO 13
<211> LENGTH: 130
<212> TYPE: PRT
<213> ORGANISM: bacteriophage fr
```

<400> SEQUENCE: 13

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130

<210> SEQ ID NO 14
<211> LENGTH: 130
<212> TYPE: PRT
<213> ORGANISM: bacteriophage GA

<400> SEQUENCE: 14

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 15
<211> LENGTH: 132
<212> TYPE: PRT
<213> ORGANISM: bacteriophage SP

<400> SEQUENCE: 15

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

```
Val Ala Ser Leu Ser Glu Ala Gly Ala Val Pro Ala Leu Glu Lys Arg
            35                  40                  45

Val Thr Val Ser Val Ala Gln Pro Ser Arg Asn Arg Lys Asn Phe Lys
     50                  55                  60

Val Gln Ile Lys Leu Gln Asn Pro Thr Ala Cys Thr Arg Asp Ala Cys
 65                  70                  75                  80

Asp Pro Ser Val Thr Arg Ser Ala Phe Ala Asp Val Thr Leu Ser Phe
                 85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
            115                 120                 125

Asn Pro Ala Tyr
        130

<210> SEQ ID NO 16
<211> LENGTH: 329
<212> TYPE: PRT
<213> ORGANISM: bacteriophage SP

<400> SEQUENCE: 16

Ala Lys Leu Asn Gln Val Thr Leu Ser Lys Ile Gly Lys Asn Gly Asp
 1               5                  10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
            35                  40                  45

Thr Val Ser Val Ala Gln Pro Ser Arg Asn Arg Lys Asn Phe Lys Val
     50                  55                  60

Gln Ile Lys Leu Gln Asn Pro Thr Ala Cys Thr Arg Asp Ala Cys Asp
 65                  70                  75                  80

Pro Ser Val Thr Arg Ser Ala Phe Ala Asp Val Thr Leu Ser Phe Thr
                 85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
            115                 120                 125

Pro Ala Tyr Trp Ala Ala Leu Leu Val Ala Ser Ser Gly Gly Gly Asp
        130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
            180                 185                 190

Gly Asp Glu Val Ser Val Thr Phe Asp Tyr Ala Leu Glu Asp Phe Leu
            195                 200                 205

Gly Asn Thr Asn Trp Arg Asn Trp Asp Gln Arg Leu Ser Asp Tyr Asp
        210                 215                 220

Ile Ala Asn Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
            260                 265                 270
```

```
Leu Asn Ile Gln Gly Asp Ala Trp Leu Asp Leu Ser Glu Val Thr Ala
        275                 280                 285

Tyr Arg Ser Tyr Gly Met Val Ile Gly Phe Trp Thr Asp Ser Lys Ser
290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser
                325

<210> SEQ ID NO 17
<211> LENGTH: 130
<212> TYPE: PRT
<213> ORGANISM: bacteriophage MS2

<400> SEQUENCE: 17

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr
    130

<210> SEQ ID NO 18
<211> LENGTH: 133
<212> TYPE: PRT
<213> ORGANISM: bacteriophage M11

<400> SEQUENCE: 18

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
        115                 120                 125
```

Leu Asn Pro Ala Tyr
    130

<210> SEQ ID NO 19
<211> LENGTH: 133
<212> TYPE: PRT
<213> ORGANISM: bacteriophage MX1

<400> SEQUENCE: 19

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
    50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
            100                 105                 110

Leu Lys Ala Leu Leu Ala Asp Pro Met Leu Ile Asp Ala Ile Asp Asn
        115                 120                 125

Leu Asn Pro Ala Tyr
    130

<210> SEQ ID NO 20
<211> LENGTH: 330
<212> TYPE: PRT
<213> ORGANISM: bacteriophage NL95

<400> SEQUENCE: 20

Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

```
Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
                260                 265                 270

Leu His Leu Met Asp Gly Ile Tyr Val Asp Leu Ala Glu Val Thr Ala
            275                 280                 285

Tyr Arg Ser Tyr Gly Met Val Ile Gly Phe Trp Thr Asp Ser Lys Ser
        290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 21
<211> LENGTH: 129
<212> TYPE: PRT
<213> ORGANISM: bacteriophage f2

<400> SEQUENCE: 21

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 22
<211> LENGTH: 128
<212> TYPE: PRT
<213> ORGANISM: bacteriophage PP7

<400> SEQUENCE: 22

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
                20                  25                  30
```

-continued

Gly Pro Leu Val Gly Arg Leu Arg Leu Thr Ala Ser Leu Arg Gln Asn
            35                  40                  45

Gly Ala Lys Thr Ala Tyr Arg Val Asn Leu Lys Leu Asp Gln Ala Asp
 50                  55                  60

Val Val Asp Cys Ser Thr Ser Val Cys Gly Glu Leu Pro Lys Val Arg
 65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
               100                 105                 110

Thr Ser Gln Val Glu Asp Leu Val Val Asn Leu Val Pro Leu Gly Arg
           115                 120                 125

<210> SEQ ID NO 23
<211> LENGTH: 131
<212> TYPE: PRT
<213> ORGANISM: bacteriophage AP205

<400> SEQUENCE: 23

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
                20                  25                  30

Leu Arg Gln Arg Val Lys Val Gly Ile Ala Glu Leu Asn Asn Val Ser
            35                  40                  45

Gly Gln Tyr Val Ser Val Tyr Lys Arg Pro Ala Pro Lys Pro Glu Gly
 50                  55                  60

Cys Ala Asp Ala Cys Val Ile Met Pro Asn Glu Asn Gln Ser Ile Arg
 65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
               100                 105                 110

Ala Gly Leu Gly Phe Leu Asp Pro Thr Ala Ala Ile Val Ser Ser Asp
           115                 120                 125

Thr Thr Ala
130

<210> SEQ ID NO 24
<211> LENGTH: 26
<212> TYPE: DNA
<213> ORGANISM: artificial sequence
<220> FEATURE:
<223> OTHER INFORMATION: G6-10

<400> SEQUENCE: 24
gggggggacg atcgtcgggg gggggg                                          26

<210> SEQ ID NO 25
<211> LENGTH: 27
<212> TYPE: DNA
<213> ORGANISM: artificial sequence
<220> FEATURE:
<223> OTHER INFORMATION: G7-10

<400> SEQUENCE: 25
ggggggggac gatcgtcggg ggggggg                                         27

<210> SEQ ID NO 26

```
<211> LENGTH: 28
<212> TYPE: DNA
<213> ORGANISM: artificial sequence
<220> FEATURE:
<223> OTHER INFORMATION: G8-10

<400> SEQUENCE: 26 gggggggga cgatcgtcgg gggggggg                                          28

<210> SEQ ID NO 27
<211> LENGTH: 29
<212> TYPE: DNA
<213> ORGANISM: artificial sequence
<220> FEATURE:
<223> OTHER INFORMATION: G9-10

<400> SEQUENCE: 27
gggggggggg acgatcgtcg gggggggg                                         29
```